US012367987B2

(12) United States Patent
Hudgins et al.

(10) Patent No.: US 12,367,987 B2
(45) Date of Patent: Jul. 22, 2025

(54) TECHNOLOGIES FOR MANAGING CAREGIVER CALL REQUESTS VIA SHORT MESSAGE SERVICE

(71) Applicant: HIll-Rom Services, Inc., Batesville, IN (US)

(72) Inventors: Darren S. Hudgins, Cary, NC (US); Philip N. Fibiger, Winter Park, FL (US); Lewin Edwards, Newburgh, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 378 days.

(21) Appl. No.: 17/540,308

(22) Filed: Dec. 2, 2021

(65) Prior Publication Data
US 2022/0189645 A1 Jun. 16, 2022

Related U.S. Application Data

(60) Provisional application No. 63/124,993, filed on Dec. 14, 2020.

(51) Int. Cl.
*G16H 80/00* (2018.01)
*G16H 40/20* (2018.01)
*H04W 4/14* (2009.01)

(52) U.S. Cl.
CPC ............. *G16H 80/00* (2018.01); *G16H 40/20* (2018.01); *H04W 4/14* (2013.01)

(58) Field of Classification Search
None
See application file for complete search history.

(56) References Cited

U.S. PATENT DOCUMENTS

| 8,183,987 B2 * | 5/2012 | Traughber | G08B 5/222 340/286.07 |
| 8,451,101 B2 * | 5/2013 | Somasundaram | G08B 21/24 340/539.18 |
| 8,669,864 B1 * | 3/2014 | Tedesco | G08B 21/02 340/539.12 |
| 9,053,708 B2 * | 6/2015 | Koch | G10L 15/1822 |

(Continued)

FOREIGN PATENT DOCUMENTS

| CN | 109448832 A | 3/2019 |
| CN | 110970137 A | 4/2020 |
| WO | 201997744 A1 | 5/2019 |

OTHER PUBLICATIONS

Keyton Weissinger, "Mobile Technology, Patient and Family Engagement, Patients: BYOD," link: http://www.engagingpatients.org/patient-and-family-engagements-2/patients-byod/, Aug. 13, 2013, Retrieved on Jun. 10, 2020; pp. 1-8.

*Primary Examiner* — Stella Higgs
(74) *Attorney, Agent, or Firm* — Barnes & Thornburg LLP

(57) ABSTRACT

A server compute device may include circuitry configured to receive a caregiver call request based on a short message service (SMS) message sent from a mobile communication device of a patient. The circuitry of the server compute device may additionally be configured to determine as a function of a mobile communication device identifier of the mobile communication device that sent the caregiver call request, a caregiver to notify. Further, the circuitry may be configured to send, to the determined caregiver, a notification of the caregiver call request.

18 Claims, 13 Drawing Sheets

(56) References Cited

U.S. PATENT DOCUMENTS

| | | |
|---|---|---|
| 9,313,623 B1 | 4/2016 | Ledet |
| 9,524,717 B2* | 12/2016 | Nolte .................. G10L 15/26 |
| 9,652,593 B1* | 5/2017 | Schoenberg ............ H04L 67/54 |
| 10,363,182 B2 | 7/2019 | Zerhusen et al. |
| 10,510,130 B2 | 12/2019 | Raheja et al. |
| 10,621,686 B2 | 4/2020 | Mazar et al. |
| 11,055,980 B2* | 7/2021 | Mazar ................ G08B 21/0211 |
| 11,894,129 B1* | 2/2024 | Dunstan ................ G16H 50/20 |
| 2005/0288965 A1* | 12/2005 | Van Eaton ............. G16H 40/20 |
| | | 705/2 |
| 2008/0018436 A1* | 1/2008 | Traughber ............. G08B 5/222 |
| | | 340/286.07 |
| 2008/0055071 A1* | 3/2008 | Chriss .................. G16H 80/00 |
| | | 340/539.12 |
| 2008/0068447 A1* | 3/2008 | Mattila .................... H04N 7/15 |
| | | 348/E7.083 |
| 2009/0048866 A1* | 2/2009 | Mahesh ................ G16H 15/00 |
| | | 705/2 |
| 2009/0113008 A1* | 4/2009 | Gonzalez ............. G16H 20/00 |
| | | 709/206 |
| 2011/0282951 A1* | 11/2011 | Akhtar .................. G16H 80/00 |
| | | 709/206 |
| 2012/0045044 A1* | 2/2012 | Woicke ............... H04M 3/5141 |
| | | 379/88.22 |
| 2012/0130742 A1* | 5/2012 | Church .................. G16H 40/67 |
| | | 705/3 |
| 2012/0179761 A1* | 7/2012 | Fuhrmann ............. G06F 3/0481 |
| | | 709/206 |
| 2013/0237770 A1* | 9/2013 | Sullivan ................ A61B 5/021 |
| | | 600/300 |
| 2014/0095210 A1* | 4/2014 | Goss ...................... G16H 10/60 |
| | | 705/3 |
| 2015/0149201 A1* | 5/2015 | Starmer, Jr. ............ G16H 50/30 |
| | | 705/2 |
| 2015/0302538 A1* | 10/2015 | Mazar ................ G08B 21/0211 |
| | | 705/2 |
| 2016/0055299 A1* | 2/2016 | Yarnell .................. G16H 10/60 |
| | | 705/2 |
| 2016/0125156 A1* | 5/2016 | Mehra ................... H04L 51/214 |
| | | 705/2 |
| 2017/0186301 A1* | 6/2017 | Vaddepally ............. H04W 4/80 |
| 2018/0197638 A1* | 7/2018 | Blanshard ............. G16H 80/00 |
| 2018/0325470 A1* | 11/2018 | Fountaine .......... G08B 21/0446 |
| 2018/0330063 A1 | 11/2018 | Viswanathan |
| 2019/0098492 A1* | 3/2019 | Shalayev ............... G16H 30/20 |
| 2019/0296987 A1* | 9/2019 | Cotton .................. G16H 80/00 |
| 2020/0019726 A1* | 1/2020 | Perecman ............... G06F 21/40 |
| 2020/0118680 A1* | 4/2020 | Rao ......................... G16H 20/10 |
| 2020/0194116 A1* | 6/2020 | Soumi .................. G16H 40/67 |
| 2020/0411179 A1* | 12/2020 | Frye ....................... H04M 7/006 |
| 2021/0103939 A1* | 4/2021 | McLean ................ G16H 40/20 |

\* cited by examiner

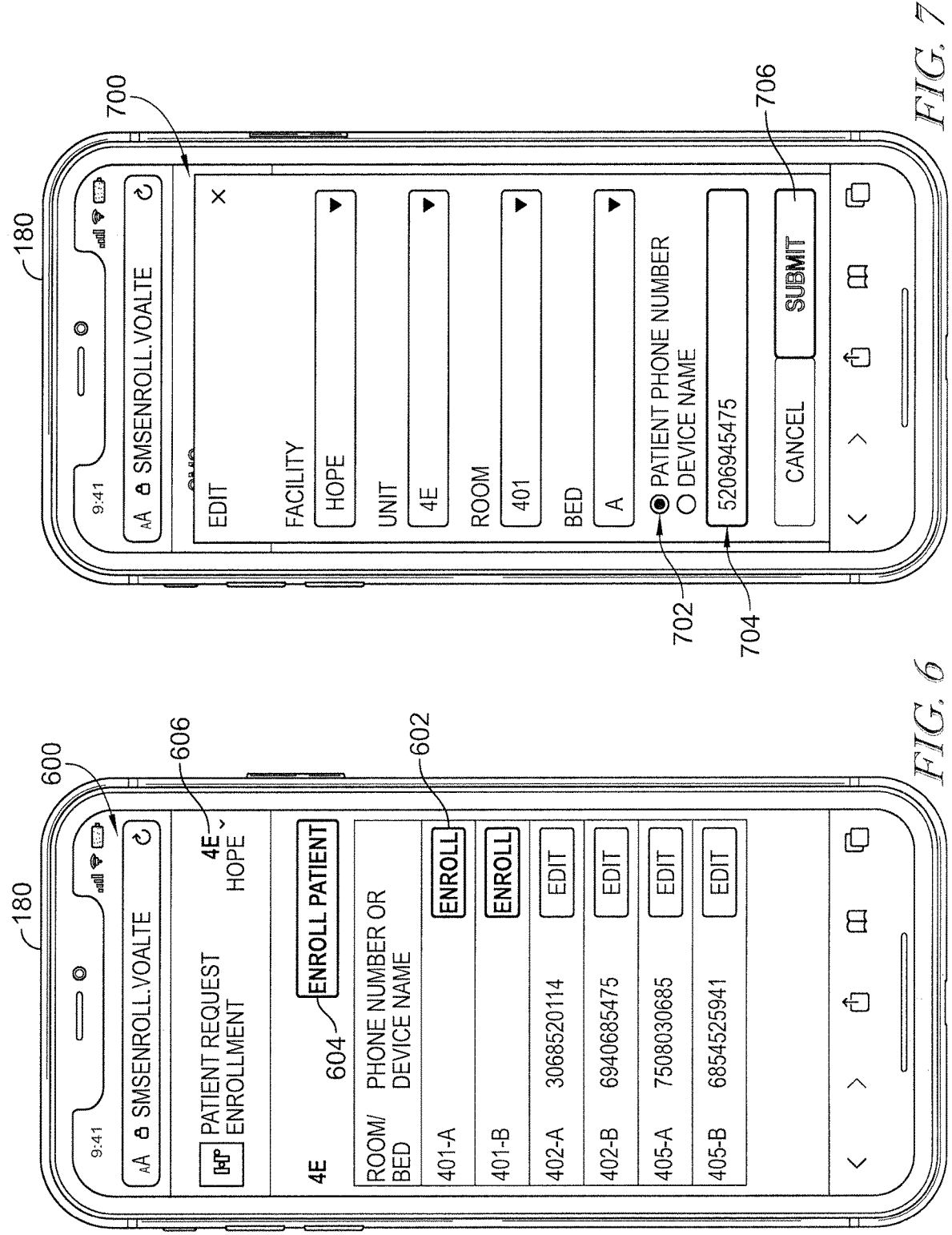

TECHNOLOGIES FOR MANAGING CAREGIVER CALL REQUESTS VIA SHORT MESSAGE SERVICE

CROSS-REFERENCE TO RELATED APPLICATION

This application claims the benefit, under 35 U.S.C. § 119(e), of U.S. Provisional Patent Application No. 63/124,993, filed Dec. 14, 2020, the entirety of which is hereby expressly incorporated by reference herein.

BACKGROUND

The present disclosure relates to coordinating patient requests for assistance in a clinical setting and particularly, to enabling caregiver call requests to be received and routed to corresponding caregivers (e.g., nurses, physicians, etc.) without the use of caregiver call hardware that is typically installed in a patient's room.

In clinical settings in which patients are cared for by caregivers, the patients are typically located in a room (e.g., on a patient support apparatus, such as a bed) and are able to request assistance on an as needed basis by utilizing caregiver call hardware located in the room (e.g., a device attached to a wall of the room and having a button or other interface element that may be activated) to initiate a call (e.g., a request for assistance) that is subsequently routed to a nurse or other caregiver. In other scenarios, the caregiver call hardware may be located elsewhere in the room, such as in the patient's bed or integrated into other equipment used to care for the patient. As such, caregiver call hardware serves as an important component in the infrastructure of a clinical setting and requires an investment of time and funds to establish. However, in emergency situations, such as pandemics, in which an unforeseen influx in patients are to be treated in a makeshift clinical setting, the time and/or funds required to set up the caregiver call hardware may be unavailable.

SUMMARY

The present application discloses one or more of the features recited in the appended claims and/or the following features which, alone or in any combination, may comprise patentable subject matter:

According to an aspect of the present disclosure, a server compute device may include circuitry configured to receive a caregiver call request based on a short message service (SMS) message sent from a mobile communication device of a patient. The circuitry may be additionally configured to determine as a function of a mobile communication device identifier of the mobile communication device that sent the caregiver call request, a caregiver to notify. Further, the circuitry may be configured to send, to the determined caregiver, a notification of the caregiver call request. In determining the caregiver to notify, the server compute device may determine a patient identifier that has been associated with the mobile communication device identifier and determine a caregiver that has been associated with that patient identifier.

In some embodiments, the circuitry in the server compute device may be configured to determine the caregiver to notify as a function of one or more words in the received caregiver call request. For example, the circuitry may identify, in the caregiver call request, a predefined word (e.g., "food" or "toilet") that is associated with a corresponding caregiver. The circuitry, in some embodiments, may determine the caregiver to notify by performing natural language processing on the word(s) in the received caregiver call request to identify a type of requested assistance and identify a corresponding caregiver that is associated with the determined type of requested assistance.

The circuitry in the server compute device may, in some embodiments, be further configured to receive a request to enroll a user in a system that enables the user to request assistance with a text message from a mobile communication device and enroll the user in response to the request. In some embodiments, the server compute device may receive the request to enroll a user based on an SMS text message sent from a cellular phone of a patient to be enrolled. The server compute device may additionally or alternatively receive the request based on an SMS text message sent from a cellular phone of a person other than the patient (e.g., a family member). In some embodiments, in receiving the request to enroll a user, the server compute device may receive a request that includes predefined text (e.g., one or more keywords) to associate an identifier of the mobile communication device with a patient identifier. The request to enroll a user may be a request to associate, with a patient identifier, a phone number of the mobile communication device that sent the request. In some embodiments, the server compute device may first send an enrollment prompt to the mobile communication device before receiving the request to enroll a user from that mobile communication device. The server compute device, in receiving the request to enroll a user, may receive a request that includes predefined text to associate an identifier of the mobile communication device with a patient identifier. The predefined text may be one or more words that have been mapped to the patient identifier (e.g., in a database accessible to the server compute device). In the illustrative embodiment, the predefined text in the enrollment request does not include the patient identifier itself. The circuitry of the server compute device, in enrolling the user, may associate (e.g., in a database) a mobile communication device identifier with a patient identifier. In associating a mobile communication device identifier with a patient identifier, the circuitry of the server compute device may associate, with the patient identifier, a phone number of the mobile communication device that send the request to enroll the user. The circuitry of the server compute device, in associating the mobile communication device identifier with a patient identifier, may associate the mobile communication device identifier (e.g., phone number) with a medical record number (MRN), a social security number, a bed number, a room number, or a name of a patient. The server compute device may associate multiple mobile communication device identifiers with a single patient identifier (e.g., enroll multiple users to be able to send text messages to initiate a caregiver call request on behalf of the same patient).

The circuitry in the server compute device may confirm the caregiver call request with the mobile communication device that sent the caregiver call request (e.g., via a text message) before sending, to the determined caregiver, a notification of the caregiver call request. In sending the notification of the caregiver call request, the server compute device may send, to a caregiver call system, a caregiver identifier for use in notifying the determined caregiver. The circuitry in the server compute device may additionally determine a caregiver communication identifier associated with the determined caregiver. In sending the notification of the caregiver call request to the determined caregiver, the circuitry in the server compute device may also send a patient identifier associated with the patient (e.g., to whom the caregiver call request pertains). The sever compute device may also send, with the notification of the caregiver call request, data indicative of the type of requested assistance. Additionally or alternatively, the circuitry in the server compute device may be configured to send a notification of the caregiver call request that includes data usable by the determined caregiver to accept the request and call the mobile communication device that sent the caregiver call request.

In some embodiments, the circuitry in the server compute device may be configured to receive a response from the caregiver and redirect the request to a backup caregiver if the response indicates a rejection of the request. The circuitry may also be configured to send, to the mobile communication device that sent the caregiver call request, a confirmation that the caregiver has been notified. In some embodiments, the circuitry may be configured to send the confirmation to multiple mobile communication devices associated with the patient (e.g., to a mobile communication device operated by the patient and to a mobile communication device operated by a family member of the patient). The circuitry in the server compute device may also be configured to receive a caregiver call request based on a textual message sent with a messaging platform that is not SMS. Further, the circuitry in some embodiments, may be configured to receive, from a mobile communication device, an unenrollment request to unenroll the user and disassociate, from a corresponding patient identifier, a mobile communication device identifier of the mobile communication device that sent the unenrollment request.

In another aspect of the present disclosure, a method may include receiving, by a server compute device, a caregiver call request based on a short message service (SMS) message sent from a mobile communication device of a patient. The method may additionally include determining, by the server compute device and as a function of a mobile communication device identifier of the mobile communication device that sent the caregiver call request, a caregiver to notify. Further, the method may include sending, by the server compute device and to the determined caregiver, a notification of the caregiver call request.

In some embodiments, in determining, as a function of a mobile communication device identifier of the mobile communication device that sent the caregiver call request, the caregiver to notify may include determining a patient identifier that has been associated with the mobile communication device identifier and determining a caregiver that has been associated with the patient identifier. The method, in some embodiments, may include determining the caregiver further as a function of one or more words in the received caregiver call request. Determining the caregiver as a function of one or more words in the received caregiver call request may, in some embodiments, include identifying a predefined word in the received caregiver call request that is associated with a corresponding caregiver. Determining the caregiver as a function of one or more words in the received caregiver call request may include performing natural language processing on the one or more words to identify a type of requested assistance and identifying a corresponding caregiver associated with the determined type of requested assistance.

In some embodiments, the method may further include receiving a request to enroll a user to request assistance with a text message from a mobile communication device and enrolling, in response to the request, the user. Receiving the request to enroll a user, in some embodiments, may include receiving the request based on an SMS text message sent from a cellular phone of a patient to be enrolled. In some embodiments, receiving the request to enroll a user may include receiving the request based on an SMS text message sent from a cellular phone of a person other than the patient. Receiving the request to enroll a user may, in some embodiments, include receiving a request that includes predefined text to associate an identifier of the mobile communication device with a patient identifier. In some embodiments, receiving the request to enroll a user may include receiving a request to associate a phone number of the mobile communication device that sent the request with a patient identifier.

In some embodiments of the method, receiving the request to enroll a user may include receiving the request in response to sending an enrollment prompt to the mobile communication device. Receiving the request to enroll a user, in some embodiments, may include receiving a request that includes predefined text to associate an identifier of the mobile communication device with a patient identifier. Receiving the request to enroll a user may include receiving a request in which the predefined text is one or more words that have been mapped to the patient identifier. In some embodiments, receiving the request to enroll a user may include receiving a request in which the predefined text does not include the patient identifier. Enrolling the user, in some embodiments, may include associating a mobile communication device identifier with a patient identifier. In some embodiments, associating a mobile communication device identifier with a patient identifier may include associating, with the patient identifier, a phone number of the mobile communication device that sent the request to enroll the user.

The method, in some embodiments, may include associating the mobile communication device identifier with a medical record number (MRN), a social security number, a bed number, a room number, or a patient name. The method may additionally include associating multiple mobile communication device identifiers with a single patient identifier. The method, in some embodiments, may include confirming the caregiver call request with the mobile communication device that sent the caregiver call request before sending, to the determined caregiver, a notification of the caregiver call request. Sending, to the determined caregiver, a notification of the caregiver call request may, in some embodiments, include sending the caregiver call request with a caregiver identifier to a caregiver call system to notify the caregiver.

In some embodiments sending, to the determined caregiver, a notification of the caregiver call request may include determining a caregiver communication device identifier associated with the determined caregiver. Sending, to the determined caregiver, a notification of the caregiver call request, in some embodiments, may include sending a notification of the caregiver call request that includes a patient identifier associated with the patient. In some embodiments, sending, to the determined caregiver, a notification of the caregiver call request may include sending a notification of the caregiver call request that includes data indicative of a type of requested assistance. Sending, to the determined caregiver, a notification of the caregiver call request may additionally or alternatively include sending a notification of the caregiver call request that includes data usable by the determined caregiver to accept the request and call the mobile communication device that sent the caregiver call request. In some embodiments, the method may additionally include receiving a response from the caregiver and redirecting the request to a backup caregiver if the response indicates a rejection of the request.

The method, in some embodiments, may further include sending, to the mobile communication device that sent the caregiver call request, a confirmation that the caregiver has been notified. The method may additionally include sending the confirmation to multiple mobile communication devices associated with the patient. In some embodiments, the method may include receiving a caregiver call request based on a textual message sent with a messaging platform that is not SMS. The method, in some embodiments, may include receiving, from a mobile communication device, an unenrollment request to unenroll the user and disassociating, from a corresponding patient identifier, a mobile communication device identifier of the mobile communication device that sent the unenrollment request.

In yet another aspect of the present disclosure, one or more computer-readable storage media may comprise a plurality of instructions that, when executed, cause a server compute device to receive a caregiver call request based on a short message service (SMS) message sent from a mobile communication device of a patient. The instructions may also cause the server compute device to determine as a function of a mobile communication device identifier of the mobile communication device that sent the caregiver call request, a caregiver to notify. Additionally, the instructions may cause the server compute device to send, to the determined caregiver, a notification of the caregiver call request.

In some embodiments, to determine, as a function of a mobile communication device identifier of the mobile communication device that sent the caregiver call request, the caregiver to notify may include to determine a patient identifier that has been associated with the mobile communication device identifier and determine a caregiver that has been associated with the patient identifier. The instructions may additionally or alternatively cause the server compute device to determine the caregiver further as a function of one or more words in the received caregiver call request. In some embodiments, to determine the caregiver as a function of one or more words in the received caregiver call request may include to identify a predefined word in the received caregiver call request that is associated with a corresponding caregiver.

To determine the caregiver as a function of one or more words in the received caregiver call request may include, in some embodiments, to perform natural language processing on the one or more words to identify a type of requested assistance and identify a corresponding caregiver associated with the determined type of requested assistance. The instructions may additionally or alternatively cause the server compute device to receive a request to enroll a user to request assistance with a text message from a mobile communication device and enroll, in response to the request, the user. In some embodiments, to receive the request to enroll a user may include to receive the request based on an SMS text message sent from a cellular phone of a patient to be enrolled.

To receive the request to enroll a user may, in some embodiments, include to receive the request based on an SMS text message sent from a cellular phone of a person other than the patient. In some embodiments, to receive the request to enroll a user may include to receive a request that includes predefined text to associate an identifier of the mobile communication device with a patient identifier. Additionally or alternatively, to receive the request to enroll a user may include to receive a request to associate a phone number of the mobile communication device that sent the request with a patient identifier. In some embodiments, to receive the request to enroll a user may include to receive the request in response to sending an enrollment prompt to the mobile communication device.

In some embodiments, to receive the request to enroll a user may include to receive a request that includes predefined text to associate an identifier of the mobile communication device with a patient identifier. To receive the request to enroll a user, in some embodiments of the one or more computer-readable storage media, may include to receive a request in which the predefined text is one or more words that have been mapped to the patient identifier. In some embodiments, to receive the request to enroll a user may include to receive a request in which the predefined text does not include the patient identifier. To enroll the user may include additionally or alternatively include to associate a mobile communication device identifier with a patient identifier. In some embodiments, to associate a mobile communication device identifier with a patient identifier may include to associate, with the patient identifier, a phone number of the mobile communication device that sent the request to enroll the user.

To associate a mobile communication device identifier with a patient identifier, may in some embodiments of the computer-readable storage media, include to associate the mobile communication device identifier with a medical record number (MRN), a social security number, a bed number, a room number, or a patient name. The instructions may additionally or alternatively cause the server compute device to associate multiple mobile communication device identifiers with a single patient identifier. Additionally or alternatively, the instructions may cause the server compute device to confirm the caregiver call request with the mobile communication device that sent the caregiver call request before sending, to the determined caregiver, a notification of the caregiver call request.

In some embodiments to send, to the determined caregiver, a notification of the caregiver call request may include to send the caregiver call request with a caregiver identifier to a caregiver call system to notify the caregiver, Additionally or alternatively, to send, to the determined caregiver, a notification of the caregiver call request may include to determine a caregiver communication device identifier associated with the determined caregiver. In some embodiments, to send, to the determined caregiver, a notification of the caregiver call request may include to send a notification of the caregiver call request that includes a patient identifier associated with the patient. Additionally or alternatively, to send, to the determined caregiver, a notification of the caregiver call request may include to send a notification of the caregiver call request that includes data indicative of a type of requested assistance.

In some embodiments, to send, to the determined caregiver, a notification of the caregiver call request may include to send a notification of the caregiver call request that includes data usable by the determined caregiver to accept the request and call the mobile communication device that sent the caregiver call request. The instructions may additionally or alternatively cause the server compute device to receive a response from the caregiver and redirect the request to a backup caregiver if the response indicates a rejection of the request. Additionally or alternatively, the instructions may cause the server compute device to send, to the mobile communication device that sent the caregiver call request, a confirmation that the caregiver has been notified. In some embodiments, the instructions may additionally or alternatively cause the server compute device to send the confirmation to multiple mobile communication devices associated with the patient. The instructions may additionally or alternatively cause the server compute device to receive a caregiver call request based on a textual message sent with a messaging platform that is not SMS. In some embodiments, the instructions may cause the server compute device to receive, from a mobile communication device, an unenrollment request to unenroll the user and disassociate, from a corresponding patient identifier, a mobile communication device identifier of the mobile communication device that sent the unenrollment request.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIGS. 5-8 are embodiments graphical user interfaces that may be displayed by a caregiver communication device to enroll a patient in the system of FIG. 1;

DETAILED DESCRIPTION

Figure 1:
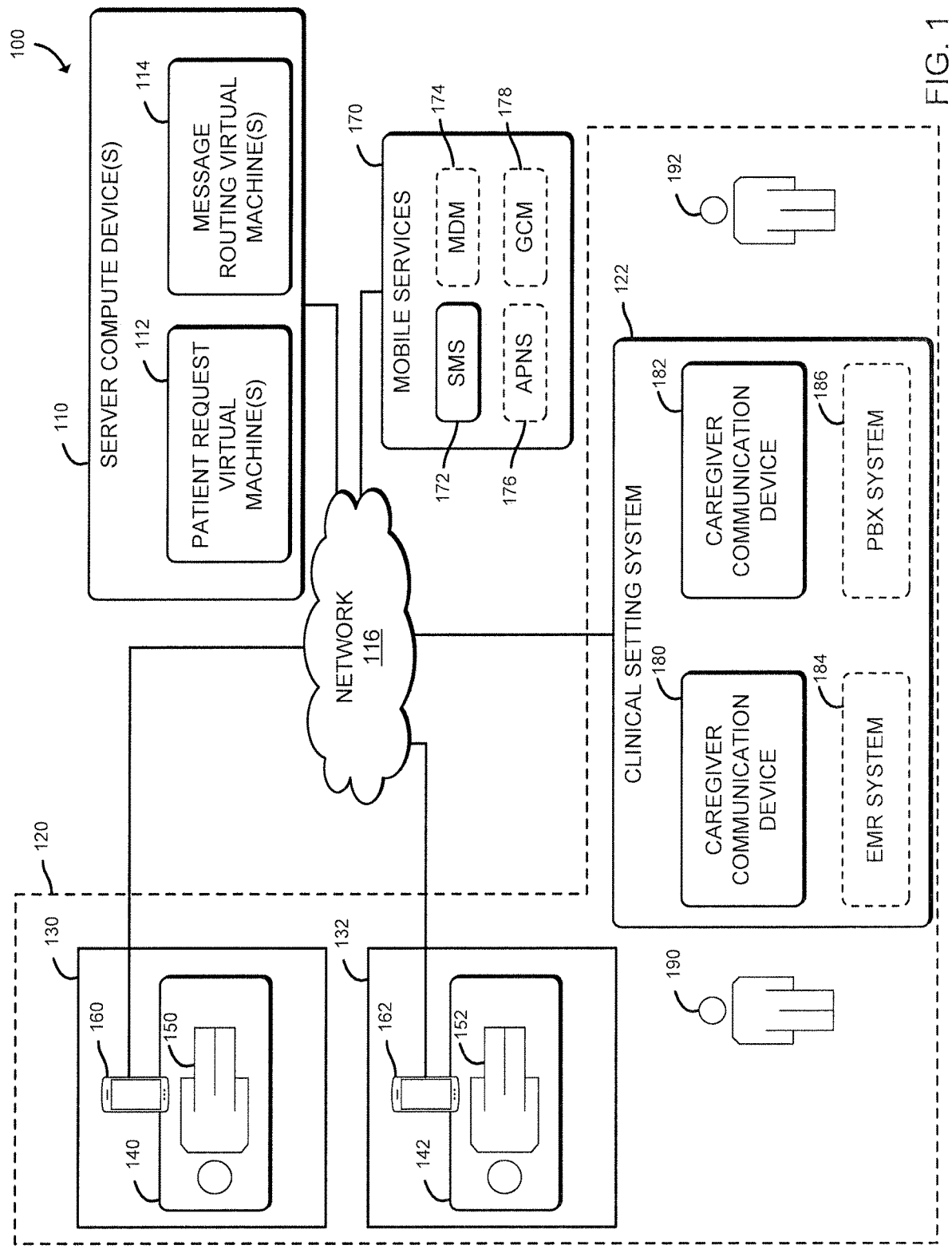
FIG. 1 is a simplified diagram of at least one embodiment of a system for managing caregiver call requests via short message service (SMS)

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims. References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a system 100 for managing caregiver call requests (also referred to herein as "patient requests") includes a set of server compute devices 110 (e.g., in a cloud datacenter) in communication with a set of mobile communication devices 160, 162 (e.g., cellular phones) of patients 150, 152 or people associated with the patients 150, 152 (e.g., relatives, guardians, etc.) and caregiver communication devices 180, 182 of a clinical setting system 122 (e.g., the set of caregiver communication devices 180, 182 and, in some embodiments, an electronic medical records (EMR) system 184, networking equipment to facilitate communications among the caregiver communication devices 180, 182, such as a private branch exchange (PBX) system 186, a wired or wireless local area network, one or more local server compute devices, etc.). The system 100, in the illustrative embodiment, additionally includes one or more providers of mobile services 170 (e.g., cellular network operators, secure messaging providers, etc.) to facilitate communication of data to and from mobile devices (e.g., the devices 160, 162, 180, 182) through a network (e.g., the network 116). The mobile services 170, in the illustrative embodiment include short message service (SMS) 172. Additionally, in some embodiments, the mobile services 170 may include mobile device management service(s) 174, Apple Push Notification service (APNs) 176 (i.e., a platform notification service created by Apple Inc. that enables third party application developers to send notification data to applications installed on Apple devices), Google Cloud Messaging (GCM) service (i.e., a mobile notification service developed by Google that enables third-party application developers to send notification data or information from developer-run servers to applications using the Google Android operating system), and/or similar services.

Each patient 150, 152, in the illustrative embodiment, is located on (e.g., resting on) a patient support apparatus (e.g., a bed) 130, 132, in a corresponding room 130, 132 of a clinical setting 120 (e.g., a building, tent, or other structure). Unlike typical clinical settings, the clinical setting 120 does not have caregiver call hardware installed in each room 130, 132, as the clinical setting 120 was established to manage an emergency (e.g., such as a pandemic), without the resources (e.g., funds, time, etc.) needed to install extensive infrastructure (e.g., a wired or wireless network and caregiver call hardware in each patient room).

In operation, the server compute device 110 enables users to use their personal mobile communication device 160, 162 to request caregiver assistance (e.g., to make a caregiver call request) using the wireless networking capabilities of their personal mobile communication device 160, 162 (e.g., connection to a cellular network) in lieu of caregiver call hardware that would otherwise be present in a clinical setting (e.g., in a hospital). To do so, the server compute device 110 may enroll a user of a mobile communication device 160, 162 in the system 100 to enable the user to submit a caregiver call (e.g., a request for assistance on behalf of a patient 150, 152). The enrollment may be initiated when the server compute device 110 receives a text message (e.g., a message sent through a short message service (SMS)) having one or more words indicative of a request to enroll, from a corresponding mobile communication device 160, 162. As described in more detail herein, the words in the text message may be a set of predefined words (e.g., previously defined as being indicative of a request to enroll a user) associated with enrolling a user with the system 100 in connection with a particular patient (e.g., 160, 162). That is, the content of the text message received by the server compute device 110, in some embodiments, may not include any identifying information of the corresponding patient (e.g., a medical record number, a social security number, etc.), but does include text that has been previously associated (e.g., in a database accessible to the server compute device 110) with enrollment of a specified patient (e.g., identified by a medical record number, a social security number, a room number, a bed number, a patient name, etc.). In the enrollment process, the server compute device 110, in the illustrative embodiment, associates (e.g., in a database) an identifier of the mobile communication device 160, 162 that sent the enrollment request (e.g., text message), such as the phone number of the mobile communication device 160, 162, with an identifier of the corresponding patient (e.g., the medical record number, social security number, room number, bed number, name, etc. of the patient).

Additionally, the server compute device 110, in response to receiving a caregiver call request (e.g., a text message) from a mobile communication device 160, 162 that has been associated with a patient 140, 142 (e.g., via the enrollment process), routes the request to a corresponding caregiver (e.g., nurse, physician, etc.) 190, 192, such as a caregiver that has been assigned to the corresponding patient (e.g., in a database accessible to the server compute device 110). In doing so, the server compute device 110 may additionally determine a type of assistance being requested (e.g., by analyzing the content of the text message for words indicative of the type of assistance, such as food, toilet, or general help) and route the request to a corresponding caregiver 190, 192 for that type of requested assistance. Additionally, as described in more detail herein, the server compute device 110 is configured to unenroll a user (e.g., disassociate an identifier of the user's mobile communication device from an identifier of the corresponding patient 150, 152) upon request (e.g., in response to a text message from the corresponding mobile communication device 160, 162 indicating a request unenroll).

Figure 2:
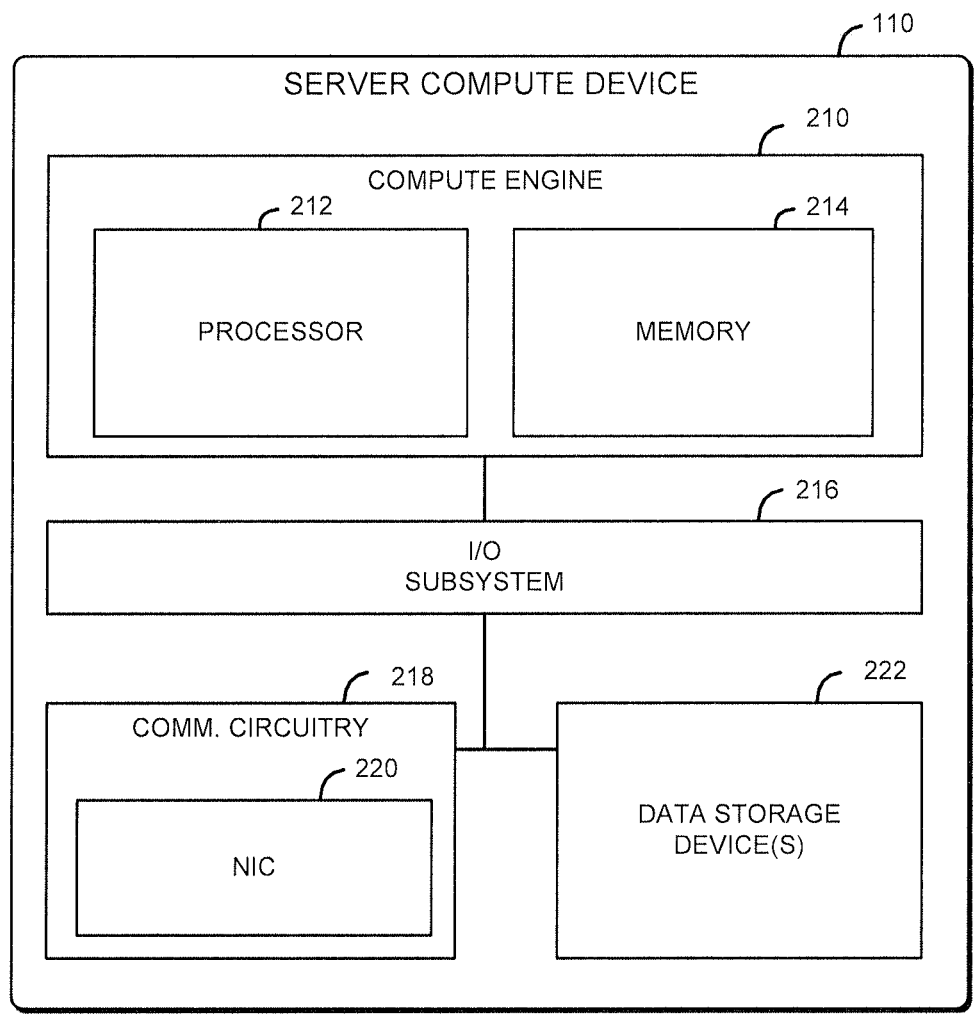
FIG. 2 is a block diagram of at least one embodiment of components of a server compute device included in the system of FIG. 1.

Referring now to FIG. 2, the illustrative server compute device 110 includes a compute engine 210, an input/output (I/O) subsystem 216, communication circuitry 218, and a data storage subsystem 222. Of course, in other embodiments, the server compute device 110 may include other or additional components, such as those commonly found in a computer (e.g., a display, peripheral devices, etc.). Additionally, in some embodiments, one or more of the illustrative components may be incorporated in, or otherwise form a portion of, another component.

The compute engine 210 may be embodied as any type of device or collection of devices capable of performing various compute functions described below. In some embodiments, the compute engine 210 may be embodied as a single device such as an integrated circuit, an embedded system, a field-programmable gate array (FPGA), a system-on-a-chip (SOC), or other integrated system or device. Additionally, in the illustrative embodiment, the compute engine 210 includes or is embodied as a processor 212 and a memory 214. The processor 212 may be embodied as any type of processor capable of performing the functions described herein. For example, the processor 212 may be embodied as a single or multi-core processor(s), a microcontroller, or other processor or processing/controlling circuit. In some embodiments, the processor 212 may be embodied as, include, or be coupled to an FPGA, an application specific integrated circuit (ASIC), reconfigurable hardware or hardware circuitry, or other specialized hardware to facilitate performance of the functions described herein.

The main memory 214 may be embodied as any type of volatile (e.g., dynamic random access memory (DRAM), etc.) or non-volatile memory or data storage capable of performing the functions described herein. Volatile memory may be a storage medium that requires power to maintain the state of data stored by the medium. In some embodiments, all or a portion of the main memory 214 may be integrated into the processor 212. In operation, the main memory 214 may store various software and data used during operation such as mobile communication device identifiers, patient identifiers, caregiver identifiers, caregiver communication devices identifiers, types of assistance each caregiver is assigned to provide, associations between the above data, applications, libraries, and drivers.

The compute engine 210 is communicatively coupled to other components of the server compute device 110 via the I/O subsystem 216, which may be embodied as circuitry and/or components to facilitate input/output operations with the compute engine 210 (e.g., with the processor 212 and the main memory 214) and other components of the server compute device 110. For example, the I/O subsystem 216 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some embodiments, the I/O subsystem 216 may form a portion of a system-on-a-chip (SoC) and be incorporated, along with one or more of the processor 212, the main memory 214, and other components of the server compute device 110, into the compute engine 210.

The communication circuitry 218 may be embodied as any communication circuit, device, or collection thereof, capable of enabling communications over a network between the server compute device 110 and another device (e.g., the mobile communication devices 160, 162, the clinical setting system 122, including the caregiver communication devices 180, 182, etc.). The communication circuitry 218 may be configured to use any one or more communication technology (e.g., wired or wireless communications) and associated protocols (e.g., Ethernet, Wi-Fi®S, WiMAX, Bluetooth®, cellular, etc.) to effect such communication.

The illustrative communication circuitry 218 includes a network interface controller (NIC) 220. The NIC 220 may be embodied as one or more add-in-boards, daughter cards, network interface cards, controller chips, chipsets, or other devices that may be used by the server compute device 110 to connect with another compute device (e.g., the mobile communication devices 160, 162, the clinical setting system 122, including the caregiver communication devices 180, 182, etc.). In some embodiments, the NIC 220 may be embodied as part of a system-on-a-chip (SoC) that includes one or more processors, or included on a multichip package that also contains one or more processors. In some embodiments, the NIC 220 may include a local processor (not shown) and/or a local memory (not shown) that are both local to the NIC 220. In such embodiments, the local processor of the NIC 220 may be capable of performing one or more of the functions of the compute engine 210 described herein. Additionally or alternatively, in such embodiments, the local memory of the NIC 220 may be integrated into one or more components of the server compute device 110 at the board level, socket level, chip level, and/or other levels.

Each data storage device 222, may be embodied as any type of device configured for short-term or long-term storage of data such as, for example, memory devices and circuits, memory cards, hard disk drives, solid-state drives, or other data storage device. Each data storage device 222 may include a system partition that stores data and firmware code for the data storage device 222 and one or more operating system partitions that store data files and executables for operating systems. While shown as a single unit, it should be appreciated that the components of the server compute device 110 may, in some embodiments, be distributed across multiple physical locations (e.g., multiple racks in a data center). Further, one or more of the components may be virtualized (e.g., in a virtual machine executing on one or more physical compute devices).

The mobile communication devices 160, 162 and the caregiver communication devices 180, 182 may have components similar to those described in FIG. 2 with reference to the server compute device 110. The description of those components of the server compute device 110 is equally applicable to the description of components of the mobile communication devices 160, 162 and the caregiver communication devices 180, 182. Further, it should be appreciated that any of the devices 160, 162, 180, 182 may include other components, sub-components, and devices commonly found in a computing device, which are not discussed above in reference to the server compute device 110 and not discussed herein for clarity of the description.

In the illustrative embodiment, the server compute device 110 and the devices 160, 162, 180, 182 are in communication via a network 116, which may be embodied as any type of wired or wireless communication network, including cellular networks (e.g., Global System for Mobile Communications (GSM), Long Term Evolution (LTE), Worldwide Interoperability for Microwave Access (WiMAX), 3G, 4G, 5G, etc.), radio area networks (RAN), global networks (e.g., the internet), local area networks (LANs) or wide area networks (WANs), digital subscriber line (DSL) networks, cable networks (e.g., coaxial networks, fiber networks, etc.), or any combination thereof, including gateways and corresponding functions (e.g., application programming interfaces, such as representational state transfer (REST) APIs, Lambda functions, etc.) between various networks (e.g., for converting a short message service (SMS) communication sent through a cellular network to one or more packets sent through the internee or a wired or wireless local area network, or vice versa).

Figure 3A:
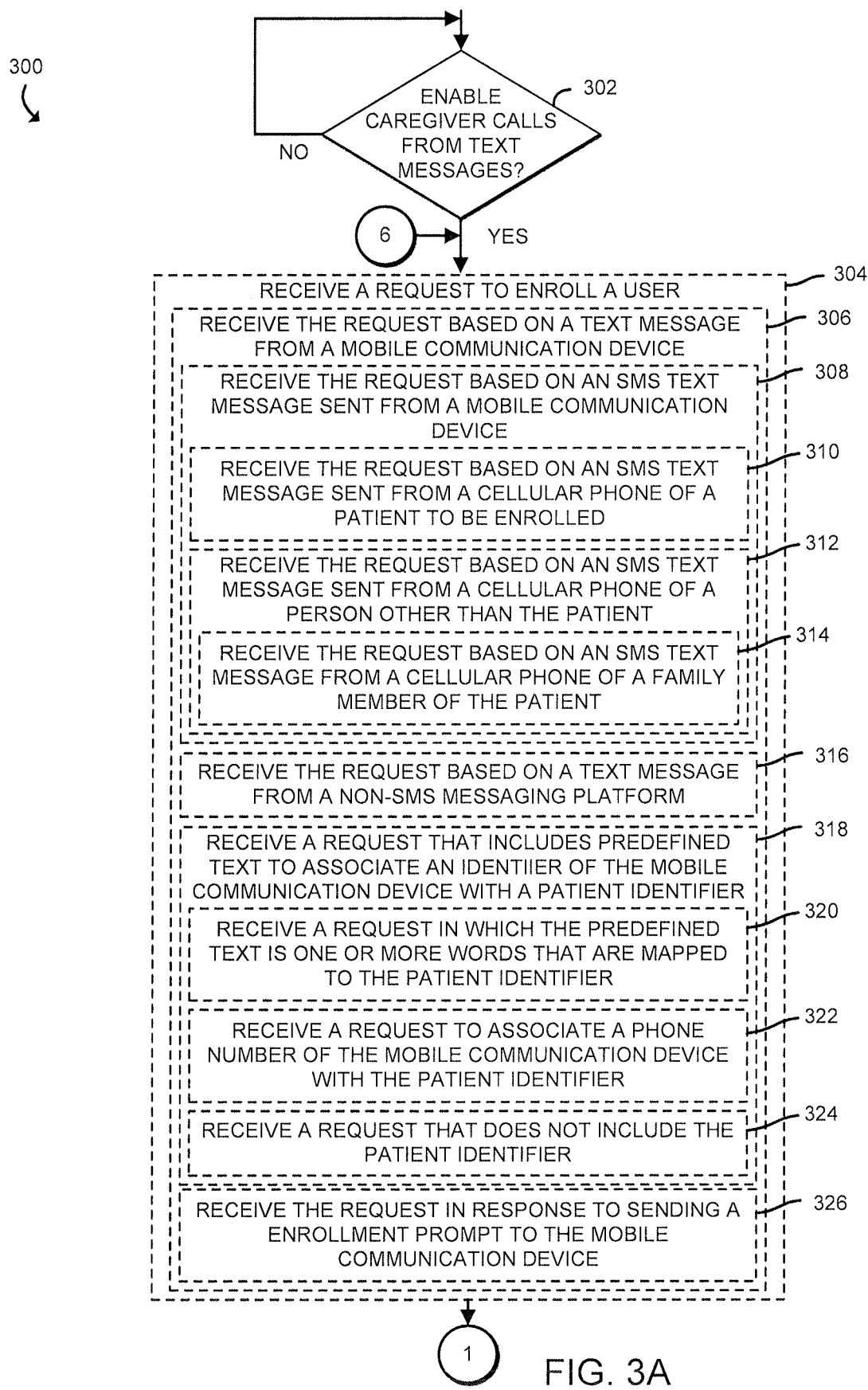
FIGS. 3A-F are simplified flow diagrams of at least one embodiment of a method for managing caregiver call requests that may be performed by the system of FIGS. 1 and 2.

Referring now to FIG. 3A, the server compute device 110, in operation, may perform a method 300 for managing caregiver call requests based on text messages (e.g., SMS messages) from mobile communication devices 160, 162. In the illustrative embodiment, the method 300 begins with block 302 in which the server compute device 110 determines whether to enable caregiver calls from text messages (e.g., to enable managing caregiver calls based on text messages, such as SMS messages). In doing so, the server compute device 110 may determine whether a request (e.g., from an administrator) has been received to enable managing caregiver calls based on text messages, whether a configuration setting (e.g., in a memory of the server compute device 110) indicates to enable managing caregiver calls based on text messages, and/or based on other factors. Regardless, in response to a determination to enable managing caregiver calls based on text messages, the method 300 advances to block 304 in which the server compute device 110 may receive a request to enroll a user.

In receiving a request to enroll a user, the server compute device 110 may receive the request based on a text message from a mobile communication device (e.g., a mobile communication device 160, 162), as indicated in block 306. In doing so, and as indicated in block 308, the server compute device 110 may receive the request based on an SMS text message sent from a mobile communication device (e.g., a mobile communication device 160, 162). For example, and as indicated in block 310, the server compute device 110 may receive the request based on an SMS text message sent from a cellular phone of a patient to be enrolled. Alternatively, the server compute device 110 may receive the request based on an SMS text message sent from a cellular phone of a person other than the patient, as indicated in block 312. For example, the server compute device 110 may receive the request based on an SMS text message sent from a cellular phone of a family member of the patient, as indicated in block 314.

In some embodiments, the server compute device 110 may receive the request based on a text message from a non-SMS messaging platform, as indicated in block 316. That is, the server compute device 110 may receive the request sent using a protocol other than short message service, such as the Apple Push Notification service (APNs), the Google Cloud Messaging (GCM) service, a messaging protocol of a Mobile Device Management (MDM) service, Rich Communication Services (RCS), the Signal protocol, or other messaging protocol. As indicated in block 318, the server compute device 110 may receive a request that includes predefined text to associate an identifier of the mobile communication device (e.g., the mobile communication device 160, 162 that sent the request) with a patient identifier. In doing so, the server compute device 110 may receive a request in which the predefined text is one or more words that are mapped to the patient identifier, as indicated in block 320. For example, the server compute device 110 may receive a request that includes a unique phrase such as "least endangered cow", which is already mapped to a particular patient identifier (e.g., medical record number, social security number, room number, bed number, etc.) in a dataset (e.g., database) accessible to the server compute device 110 (e.g., in the memory 214 or a data storage device 222).

As indicated in block 322, the server compute device 110 may receive a request to associate a phone number of the mobile communication device with the patient identifier (e.g., the mobile communication device identifier is a phone number). In the illustrative embodiment, the server compute device 110 receives a request that does not include the patient identifier itself (e.g., the content of the request does not include the patient identifier anywhere), as indicated in block 324. As indicated in block 326, the server compute device 110 may receive the request in response to sending an enrollment prompt (e.g., a message to prompt the recipient to send an enrollment request) to the mobile communication device 160, 162. For example, the enrollment request sent to the mobile communication device 160, 162 may be "text Least Endangered Cow to 904 to enroll."

Figure 3B:
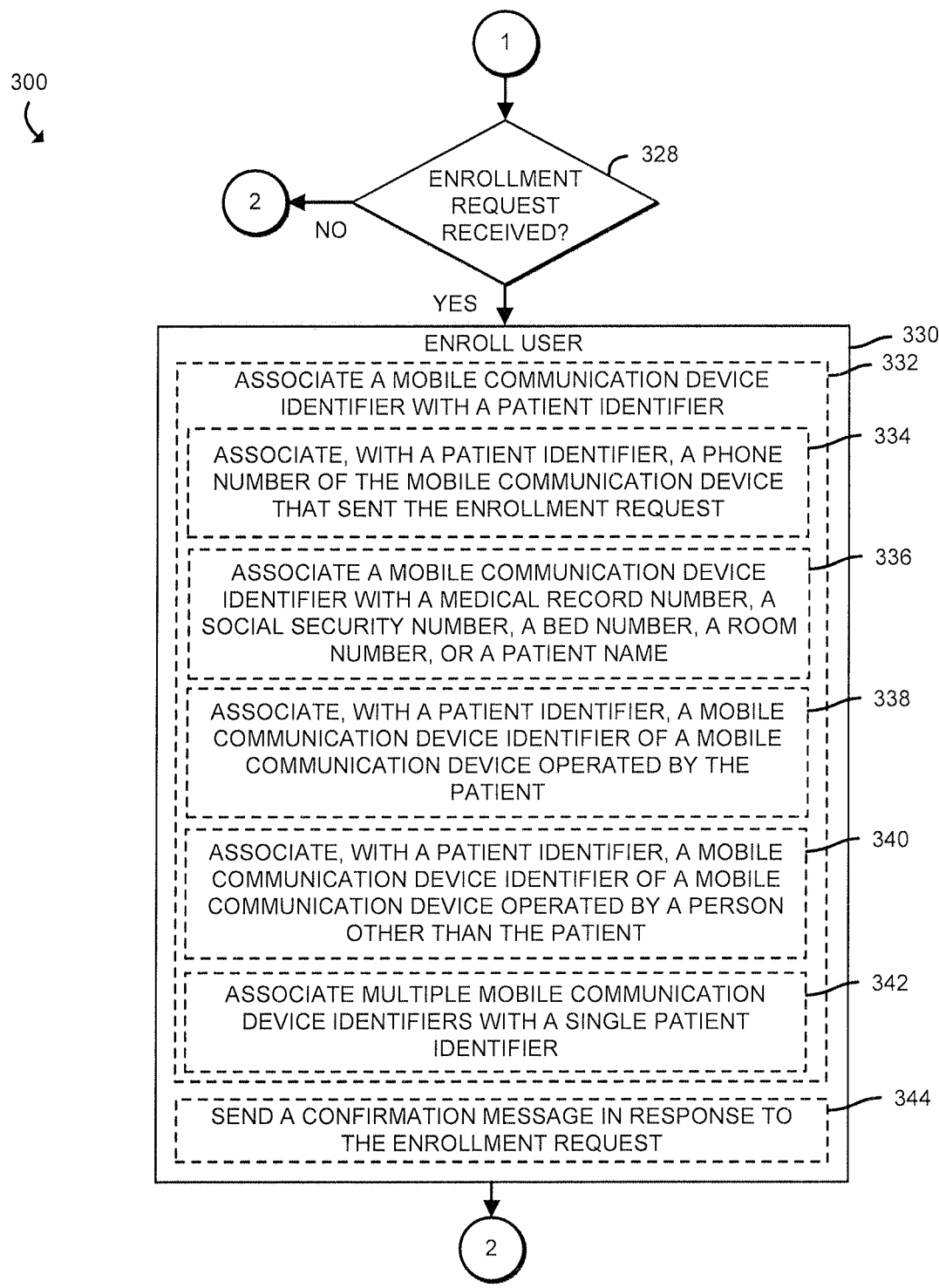

Referring now to FIG. 3B, the server compute device 110 determines a subsequent course of action based on whether an enrollment request has been received, as indicated in block 328. If not, the method 300 advances to block 346 of FIG. 3C, in which the server compute device 110 may receive a caregiver call request based on a textual message sent from a mobile communication device 160, 162, as described in more detail herein. Otherwise, if an enrollment request has been received, the method 300 advances to block 330, in which the server compute device 110 enrolls a user. In doing so, the server compute device 110, in the illustrative embodiment, associates (e.g., stores data indicative of a relationship) a mobile communication device identifier with a patient identifier, as indicated in block 332. As indicated in block 334, in the illustrative embodiment, the server compute device 110, associates, with a patient identifier, a phone number of the mobile communication device that sent the enrollment request. In making the association, the server compute device 110 may associate the mobile communication device identifier (e.g., phone number) with a medical record number, a social security number, a bed number, a room number, and/or a patient name, as indicated in block 336.

The server compute device 110, in associating a mobile communication device identifier with a patient identifier, may associate, with the patient identifier, a mobile communication device identifier of a mobile communication device operated by the patient, as indicated in block 338 and/or may associate, with the patient identifier, a mobile communication device identifier of a mobile communication device other than the patient (e.g., a family member of the patient or other person who will send text messages (e.g., SMS text messages) to initiate a caregiver call on behalf of the patient), as indicated in block 340. As indicated in block 342, the server compute device 110 may associate multiple mobile communication device identifiers (e.g., multiple phone numbers) with a single patient identifier. Additionally, and as indicated in block 344, the server compute device 110 may send a confirmation message (e.g., to the mobile communication device 160, 162 that sent the enrollment request) in response to the enrollment request (e.g., indicating that request has been received and that enrollment process has been executed). In some embodiments, enrollment of a patient may be initiated using software operated by a caregiver or other personnel, rather than being initiated by the patient, as described in more detail herein with reference to FIGS. 5-8.

Figure 3C:
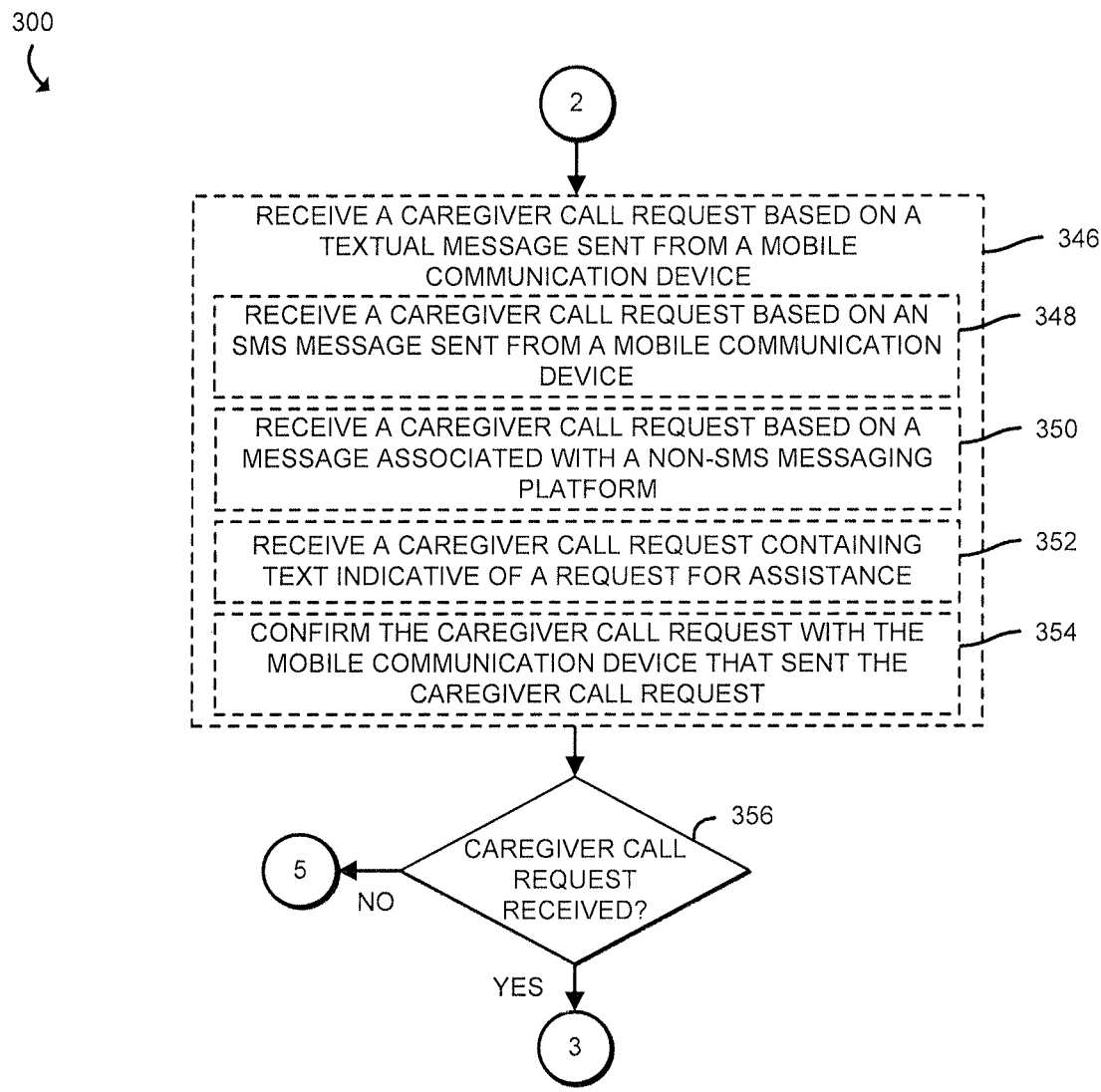

Referring now to FIG. 3C, as indicated in block 346, the server compute device 110 may receive a caregiver call request based on a textual message sent from a mobile communication device (e.g., a mobile communication device 160, 162 that has been associated with a patient identifier through the enrollment process described with reference to FIGS. 3A and 3B). In doing so, the server compute device 110 may receive a caregiver call request based on an SMS message sent from a mobile communication device (e.g., a mobile communication device 160, 162), as indicated in block 348. Alternatively, the server compute device 110 may receive a caregiver call request based on a message associated with (e.g., sent using) a non-SMS messaging platform (e.g., the Apple Push Notification service (APNs), the Google Cloud Messaging (GCM) service, a messaging protocol of a Mobile Device Management (MDM) service, Rich Communication Services (RCS), the Signal protocol, or other messaging protocol), as indicated in block 350. In the illustrative embodiment, and as indicated in block 352, the server compute device 110 receives a caregiver call request that includes text indicative of a request for assistance.

In some embodiments, in response to receiving the caregiver call request, the server compute device 110 confirms, with the mobile communication device 160, 162 that sent the request, that the user intended to send a caregiver call request (e.g., by sending a text message to the mobile communication device 160, 162 asking the user to enter a specified response to confirm the request, or prompting the user to cancel the request within a specified period of time by responding with a particular message, such as "cancel" or "X" to cancel the request, and receiving a corresponding response), as indicated in block 354. Afterwards, in block 356, the server compute device 110 determines the subsequent course of action as a function of whether a caregiver call request was received. If a caregiver call request was not received in block 346, then the method 300 advances to block 392 of FIG. 3F, in which the server compute device 110 may receive an unenrollment request, as described in more detail herein. Otherwise, if a caregiver call request was received in block 346, the method 300 advances to block 358 of FIG. 3D, in which the server compute device 110 determines, as a function of a mobile communication device identifier of the mobile communication device that sent the caregiver call request, a caregiver to notify. The mobile communication device identifier, in the illustrative embodiment, is provided to the server compute device 110 (e.g., via the network 116, and, in some embodiments, through one or more gateway devices that convert communications from one protocol to another) with the text message itself (e.g., as metadata, as a parameter to a function exposed by the server compute device 110 for receiving a text message sent by a mobile communication device, etc.).

Figure 3D:
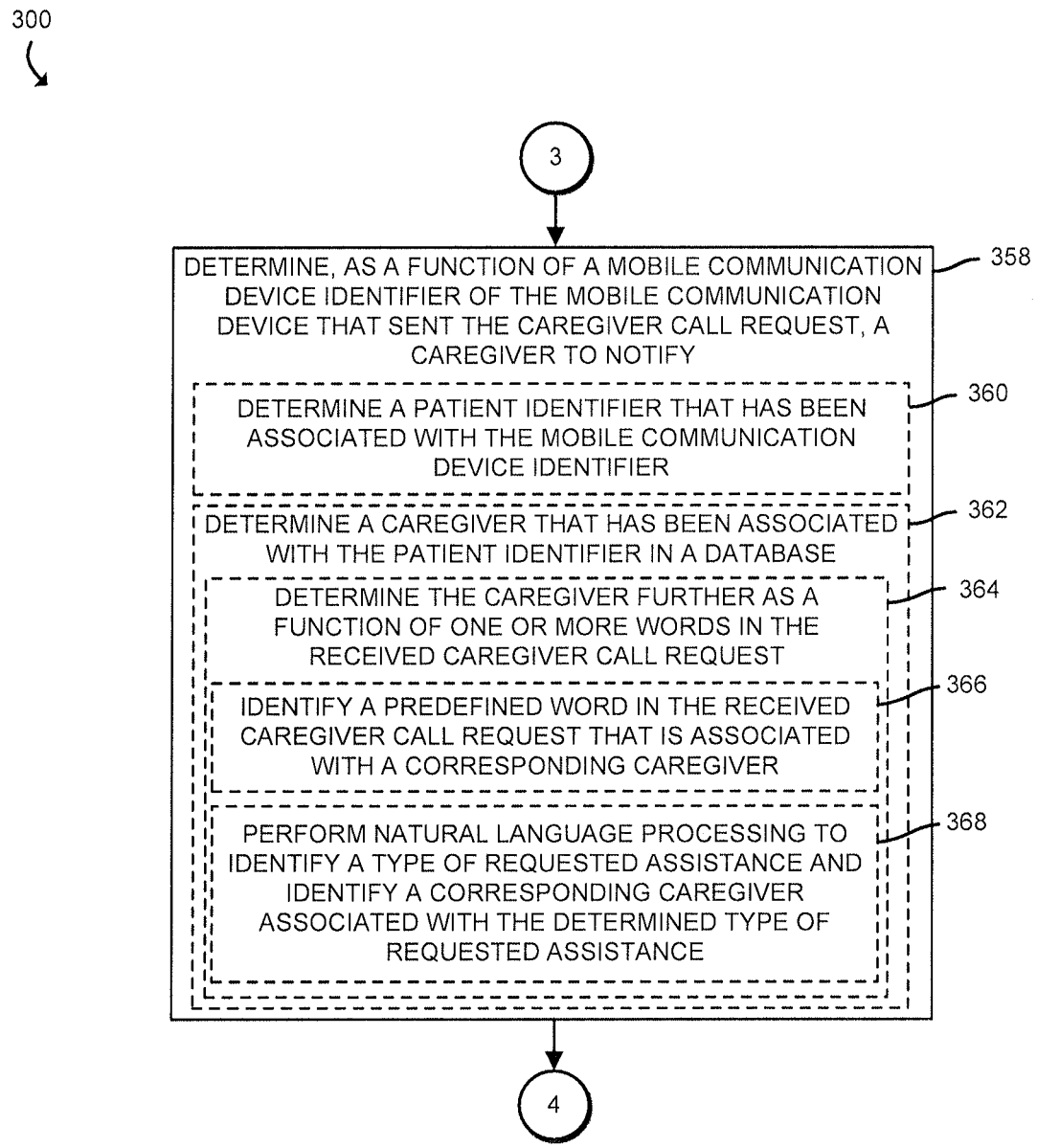

Still referring to FIG. 3D, in determining a caregiver to notify, the server compute device 110, in the illustrative embodiment, determines a patient identifier that has been associated with the mobile communication device identifier (e.g., based on an association that was stored in the enrollment process), as indicated in block 360. As indicated in block 362, the server compute device 110, in the illustrative embodiment, determines a caregiver that has been associated with the patient identifier in a database (e.g., in the data storage 222). In doing so, and as indicated in block 364, the server compute device 110 determines the caregiver further as a function of one or more words in the received caregiver call request. For example, and as indicated in block 366, the server compute device 110 may identify a predefined word (e.g., a key word) in the received caregiver call request that is associated with a corresponding caregiver (e.g., "food" is associated with one caregiver assigned to the patient, "toilet" is associated with another caregiver assigned to the patient, and "help" is associated with yet another caregiver assigned to the patient in a database).

Alternatively, rather than identifying predefined words associated with corresponding caregivers in a database, the server compute device 110 may perform natural language processing (e.g., using a trained neural network) on the text of the caregiver call request to identify a type of requested assistance and then identify a corresponding caregiver associated with the determined type of requested assistance (e.g., from a database similar to that described with reference to block 366), as indicated in block 368. In some embodiments, the server compute device 110 may determine a priority level associated with the caregiver call request based on the content of the request. For example, the server compute device 110 may increase the priority level (e.g., from a default or normal priority level) based on a determination that the content of the request includes one or more predefined words or symbols associated (e.g., in data storage 222) with a high priority (e.g., any of the words "urgent", "now", "immediately" or synonyms thereof, or a symbol such as an exclamation point). Subsequently, the method 300 advances to block 370 of FIG. 3E, in which the server compute device 110 sends a notification of the caregiver call request (e.g., the caregiver call request and, in some embodiments, additional information to assist in routing and/or responding to the caregiver call request) to the determined caregiver 190, 192.

Figure 3E:
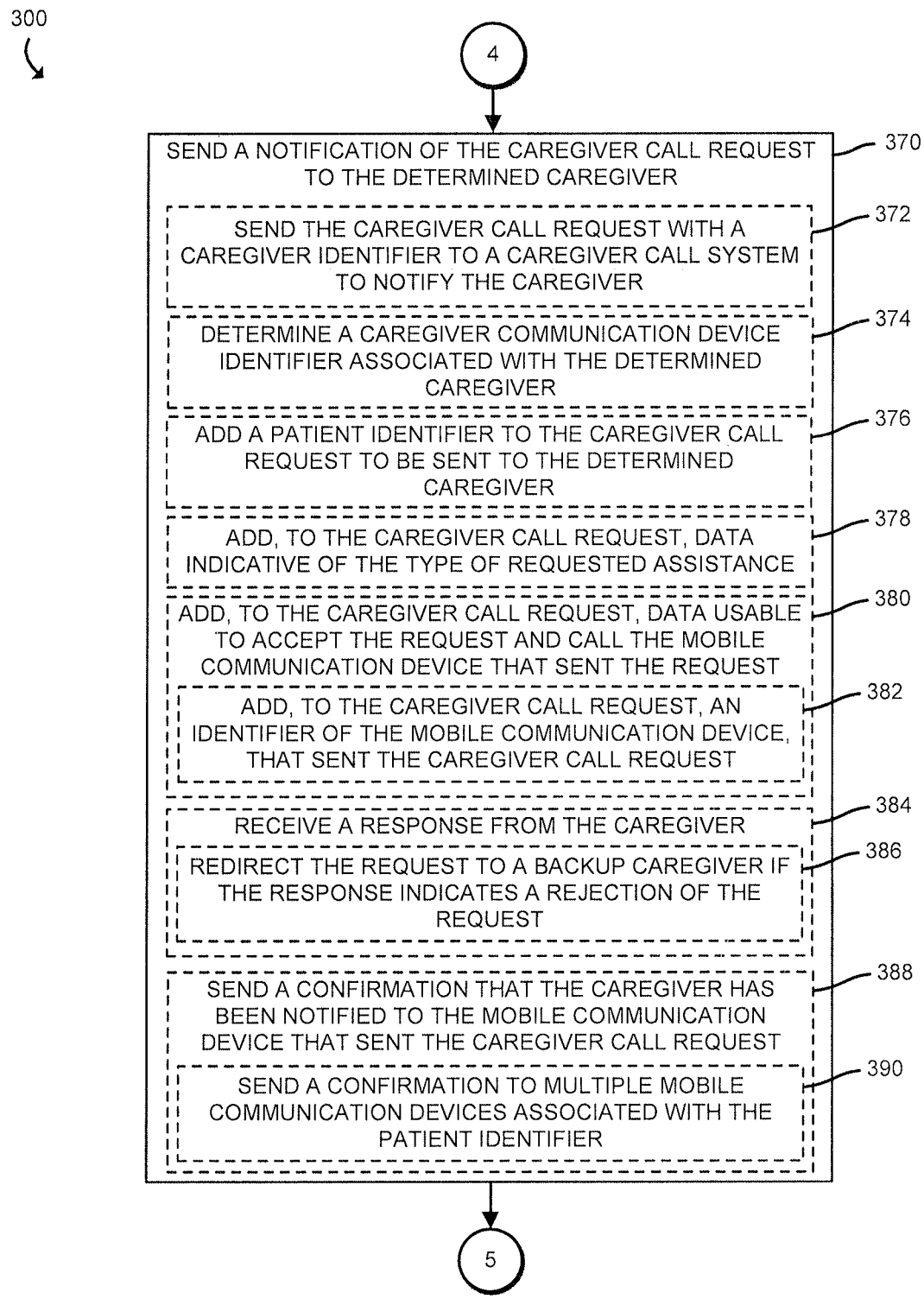

Referring now to FIG. 3E, in sending a notification of the caregiver call request, the server compute device 110 may send the caregiver call request with a caregiver identifier (e.g., any data that uniquely identifies a caregiver 190, 192) to a caregiver call system (e.g., the clinical setting system 122) to notify the corresponding caregiver 190, 192 (e.g., the caregiver determined in block 358 of FIG. 3D), as indicated in block 372. In some embodiments, the server compute device 110 may determine a caregiver communication device identifier (e.g., any data that identifies a caregiver communication device 180, 182, such as a phone number, a network address, etc.) associated with the determined caregiver 190, 192 (e.g., in a database that associates caregiver identifiers with caregiver communication device identifiers), as indicated in block 374. The server compute device 110 may, in some embodiments, assist in routing the caregiver call request to the caregiver communication device 180, 182 used by the determined caregiver 190, 192, such as by sending the caregiver communication device identifier to the clinical setting system 122. As indicated in block 376, the server compute device 110 may add a patient identifier (e.g., indicative of the patient for whom assistance was requested) to the caregiver call request to be sent to the determined caregiver. The server compute device 110 may also add, to the caregiver call request, data indicative of the type of requested assistance (e.g., a code or word(s) indicative of the type of requested assistance), as indicated in block 378. In some embodiments, a caregiver call request may have a priority that is higher than a default or normal priority, as described above. The system 100, in some embodiments, may vary the presentation of a caregiver call request as a function of the priority of the request. For example, the system 100 may cause a caregiver's mobile communication device 160 to emit a different sound for a high priority request than a normal priority request. In some embodiments, the system 100 may cause the caregiver's mobile communication device 160 to emit a sound even if the caregiver has placed the mobile communication device 160 in a silent or do not disturb mode. Further, in some embodiments, the system 100 may initiate an alert mode associated with a color in one or more caregiver alert systems (e.g., devices capable of illuminating with a selected color) present in the clinical setting 120 (e.g., near the doorway to the patient's room).

In some embodiments, the server compute device 110 may add, to the caregiver call request, data usable (e.g., by the caregiver communication device 180, 182) to accept the request and call the mobile communication device 160, 162 that initially sent the request (e.g., the SMS message), as indicated in block 380. For example, the server compute device 110 may include, in the caregiver call request, code to present a user interface element (e.g., a button, a link, etc.) that, when activated (e.g., by the corresponding caregiver 190, 192), sends an acceptance message back to the server compute device 110 and initiates a voice call to the phone number of the mobile communication device 160, 162 that initiated the caregiver call request. In doing so, the server compute device 110 may add, to the caregiver call request sent to the caregiver communication device 180, 182, an identifier (e.g., phone number) of the mobile communication device that initially sent the caregiver call request (e.g., with an SMS message), as indicated in block 382. In block 384, the server compute device 110 may receive a response (e.g., an acceptance or rejection) from the caregiver 190, 192. As indicated in block 386, the server compute device 110 may redirect the request to a backup caregiver 190, 192 (e.g. a secondary caregiver assigned to the patient) if the response indicates a rejection of the caregiver call request.

The server compute device 110, in the illustrative embodiment, also sends, to the mobile communication device 160, 162 that initially sent the caregiver call request, a confirmation that the caregiver has been notified of the request, as indicated in block 388. In some embodiments, the server compute device 110 sends the confirmation to multiple mobile communication devices, such as every mobile communication device that has been associated with the patient (e.g., via the enrollment process described with reference to FIGS. 3A and 3B), as indicated in block 390. Subsequently, the method 300 advances to block 392 of FIG. 3F, in which the server compute device 110 may receive an unenrollment request to unenroll a user from the system 100. The types of notifications that the server compute device 110 sends to the patient may vary across embodiments, and may include, for example, (a) a notification of when the caregiver responds to the alert, (b) a message indicative of what the response was (e.g., accept/decline/other), (c) the location (e.g., via a real time location system) of the caregiver and the name of the caregiver who responded (e.g., "Nurse Smith responded, s/he is in Ward 12 right now and will be with you soon"), and/or (d) free-form text from the caregiver (e.g., "Hi Mrs. Jones—I'll be a couple of minutes but you're my next patient"). Additionally or alternatively, in some embodiments, the server compute device 110 may automatically escalate a caregiver call request due to non-response or rejection of the caregiver call request by the initial recipient (e.g., "Nurse Smith couldn't answer. Your call has been escalated to Nurse Jones").

Figure 3F:
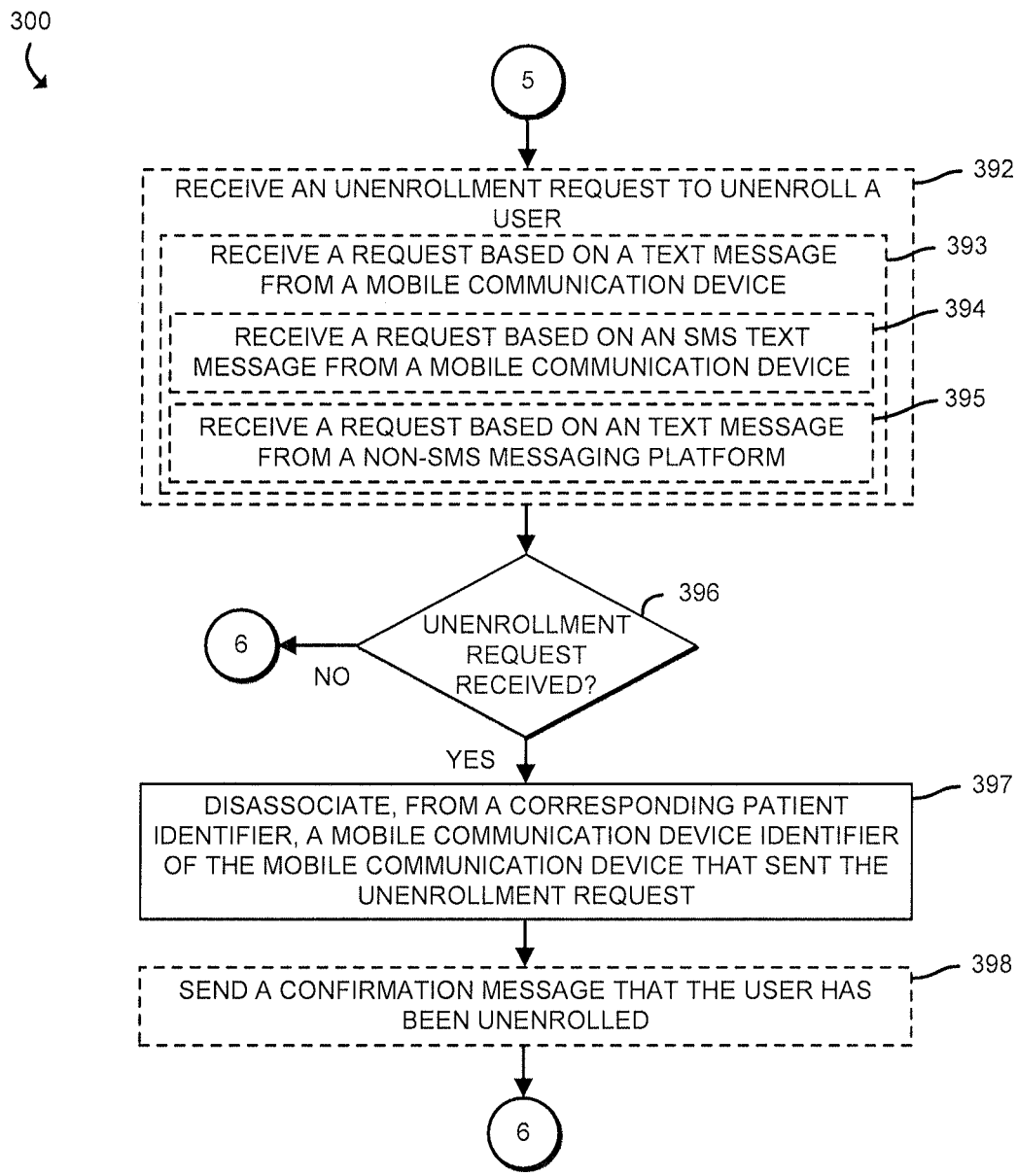

Referring now to FIG. 3F, in receiving an unenrollment request, the server compute device 110, in the illustrative embodiment, receives the request based on a text message from a mobile communication device 160, 162, as indicated in block 393. In the illustrative embodiment, the server compute device 110 receives the unenrollment request based on an SMS text message sent from a mobile communication device 160, 162, as indicated in block 394. In other embodiments, the server compute device 110 receives the request based on a text message sent through a non-SMS messaging platform (e.g., the Apple Push Notification service (APNs), the Google Cloud Messaging (GCM) service, a messaging protocol of a Mobile Device Management (MDM) service, Rich Communication Services (RCS), the Signal protocol, or other messaging protocol), as indicated in block 395.

In block 396, the server compute device 110 determines a subsequent course of action based on whether an unenrollment request was received. If not, the method 300 loops back to block 304 of FIG. 3A, in which the server compute device 110 may receive another enrollment request. Otherwise, the method 300 advances to block 397, in which the server compute device 110 disassociates (e.g., removes, from a database, data indicative of an association) from a corresponding patient identifier, the mobile communication device identifier (e.g., phone number) of the mobile communication device 160, 162 that send the unenrollment request. As indicated in block 398, the server compute device 110 may send a confirmation message (e.g., to the corresponding mobile communication device 160, 162, indicating that the user associated with that mobile communication device 160, 162 has been unenrolled from the system 100). Subsequently, the method 300 loops back to block 304 of FIG. 3A, in which the server compute device 110 may receive another enrollment request. While the operations of the method 300 have been described in a particular order for clarity, it should be understood that the operations could be performed in a different order or concurrently (e.g., the enrollment operation may be performed for a new user while a caregiver call request is concurrently being processed for another user of the system 100).

Figure 4:
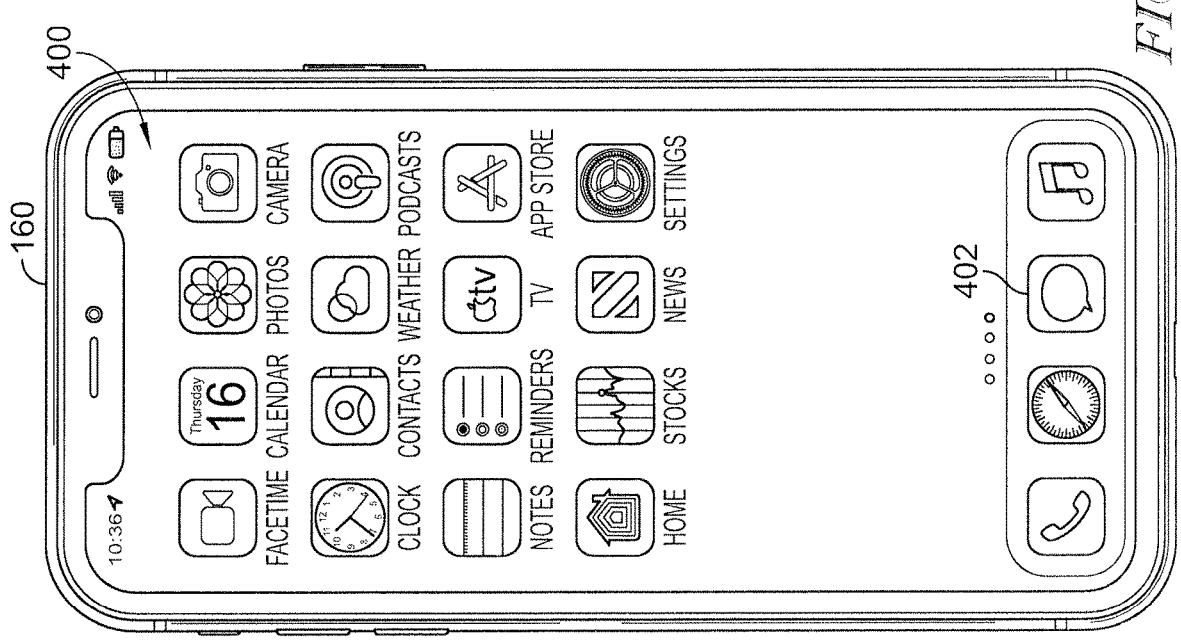
FIG. 4 is an embodiment of a graphical user interface that may be displayed by a patient mobile communication device of the system of FIG. 1 to enable access to a messaging application.

Referring now to FIG. 4, an embodiment of a graphical user interface 400 presented by a mobile communication device (e.g., the mobile communication device) 160 of a patient (e.g., the patient 150) is shown. The graphical user interface 400 includes a selectable icon 402, which, when selected (e.g., touched), activates a messaging application. The messaging application enables communication (e.g., through the SMS service 172) with the server compute device 110 and clinical setting system 122. In the illustrative embodiment, the messaging application is an SMS messaging application that is preinstalled on the mobile compute device 160. In other embodiments, the messaging application may be installed by the patient 150 or other user of the mobile compute device 160 and may communicate through a communication protocol other than SMS (e.g., RCS, the Signal protocol, APNs, GCM, an MDM communication protocol, etc.).

Figure 5:
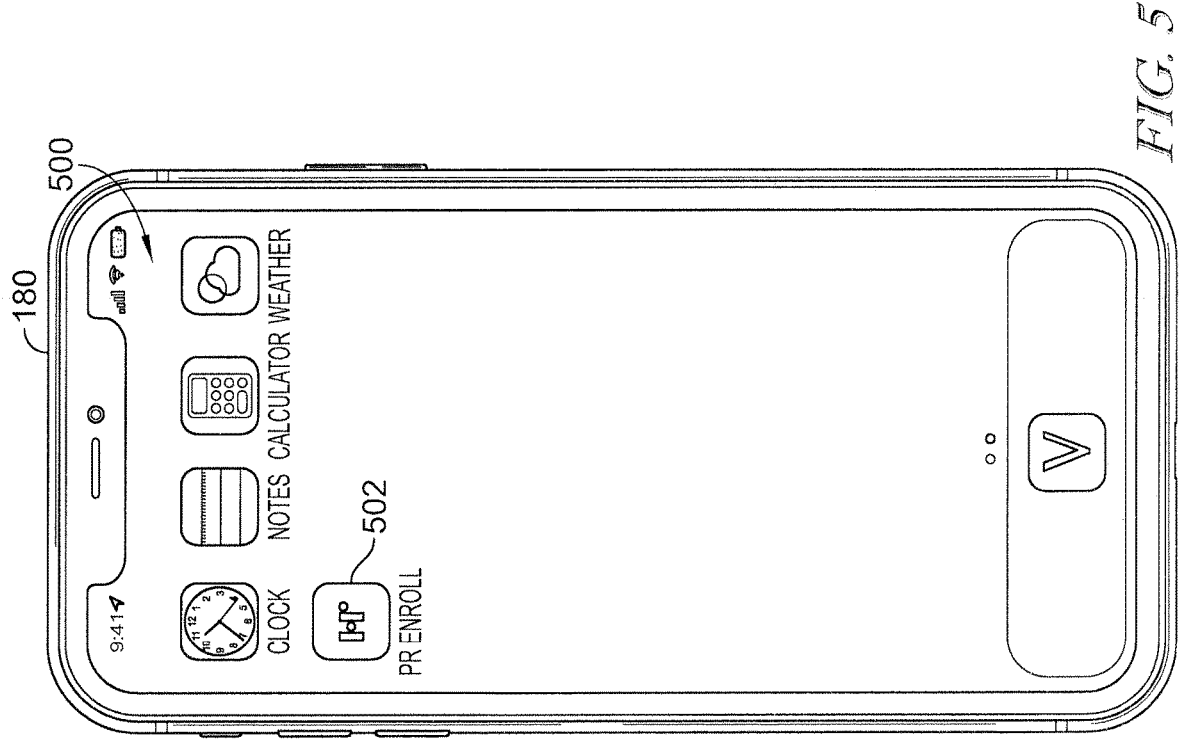

Referring to FIG. 5, a graphical user interface 500 displayed by a caregiver communication device (e.g., the caregiver communication device 180) includes a selectable icon 502. In response to detecting selection of the icon 502, the caregiver communication device 180 activates a corresponding patient enrollment application (e.g., a locally executed application, a web browser interface to a website, etc.). Referring now to FIG. 6, a graphical user interface 600 associated with the patient enrollment application includes, among other elements, a selectable enroll button 602, a selectable enroll patient button 604, and a selectable drop down element 606. The caregiver 190 may change the present location by selecting the drown down element 606 and selecting a different location presented in a list of available locations. Further, the caregiver 190 may enroll a patient in association with a room/bed that is not presently displayed in the graphical user interface 600 by selecting the enroll patient button 604. However, in an example enrollment process described in more detail herein, a caregiver (e.g., the caregiver 190) selects (e.g., touches) the selectable enroll button 602 next to a patient's (e.g., the patient 150) room number. In response to detecting selection of the enroll button 602, the caregiver communication device 180, in the illustrative embodiment, displays the graphical user interface 700 of FIG. 7.

Figure 8:
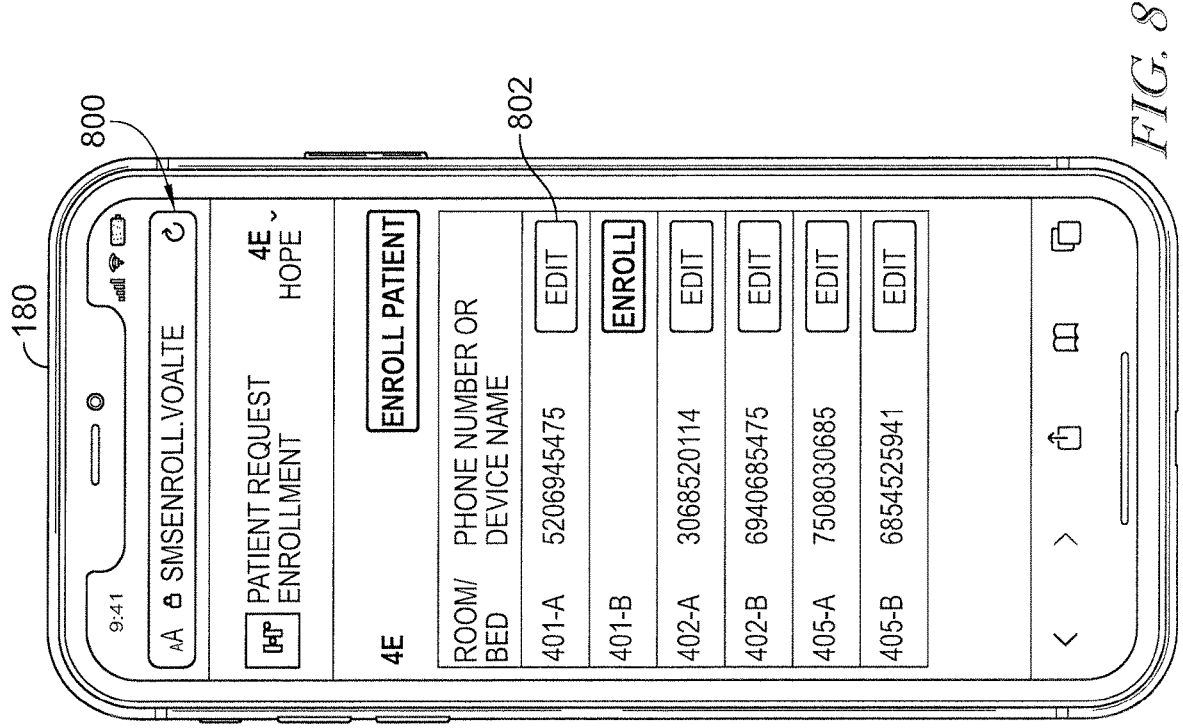

Referring now to FIG. 7, the graphical user interface 700 includes, among other elements, a selectable option button (i.e., radio button) 702, a text field 704 to receive a phone number associated with the phone number of the mobile communication device 160 of the patient 150 to be enrolled (e.g., the patient 150 in room/bed 401-A), and a selectable submit button 706. Continuing the illustrative enrollment process, the caregiver 190 selects the option button 702, enters phone number of the mobile communication device 160 of the patient 150 in the text field 704, and selects the submit button 706. In response, the caregiver communication device 180 displays the graphical user interface 800 of FIG. 8. Referring now to FIG. 8, the graphical user interface 800 is similar to the graphical user interface 600 of FIG. 6, except the enroll button 602 has been replaced with an edit button 802. As such, the graphical user interface 800 indicates that the patient 150 associated with room/bed 401-A has been enrolled and that information associated with the patient 150, such as the phone number of the patient's mobile communication device 160 may be edited in a graphical user interface similar to the graphical user interface 700 of FIG. 7 upon selection of the edit button 802. The system 100, in response to enrollment of the patient 150, may send a message (e.g., an SMS message) confirming that the patient has been enrolled.

Figure 9:
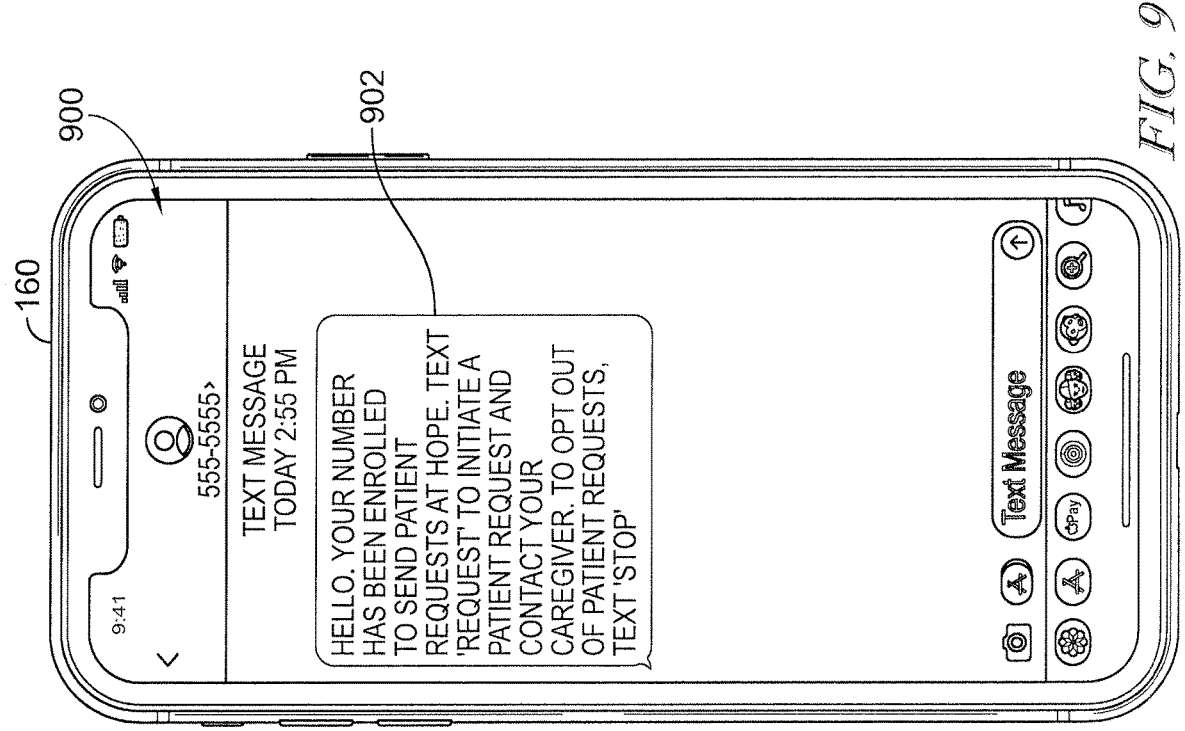
FIGS. 9-10 are embodiments of graphical user interfaces that may be displayed by a patient mobile communication device to confirm enrollment in the system of FIG. 1 and to submit a caregiver call request.

Referring now to FIG. 9, the mobile communication device 160, in response to receiving a message (e.g., an SMS message) confirming enrollment of the patient 150, displays a graphical user interface 900 within the messaging application. The graphical user interface 900 includes a representation 902 of the message confirming enrollment of the user. As shown, the representation 902 of the message indicates that the phone number associated with the patient 150 has been enrolled to send patient requests at the present location (e.g., "HOPE") and includes instructions for initiating a patient request (e.g., text "REQUEST") and for opting out of patient requests (e.g., text "STOP").

Figure 10:
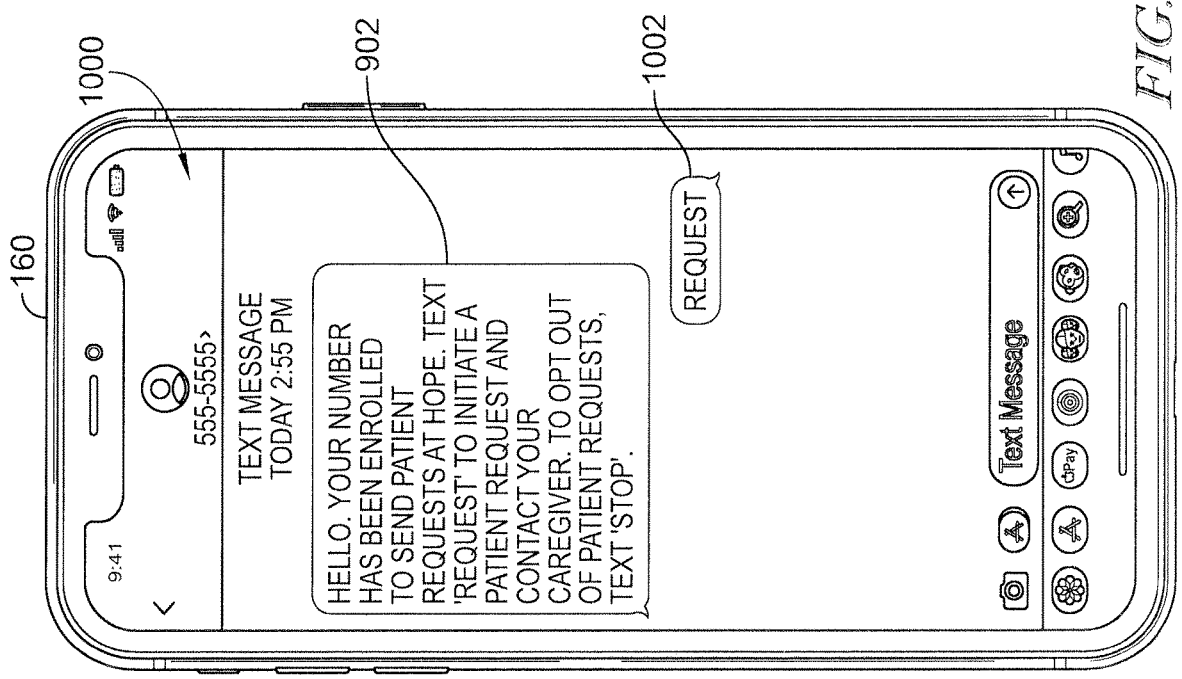

Referring now to FIG. 10, a graphical user interface 1000, similar to the graphical user interface 900, includes a representation 1002 of a text message submitted by the patient 150, in response to the confirmation message described above. As indicated in the representation 1002, the patient 150 has submitted a text message containing the word "REQUEST". In response, the system 100 notifies the caregiver communication device 180 of the request and the caregiver communication device 180 displays the graphical user interface 1100 of FIG. 11.

Figure 11:
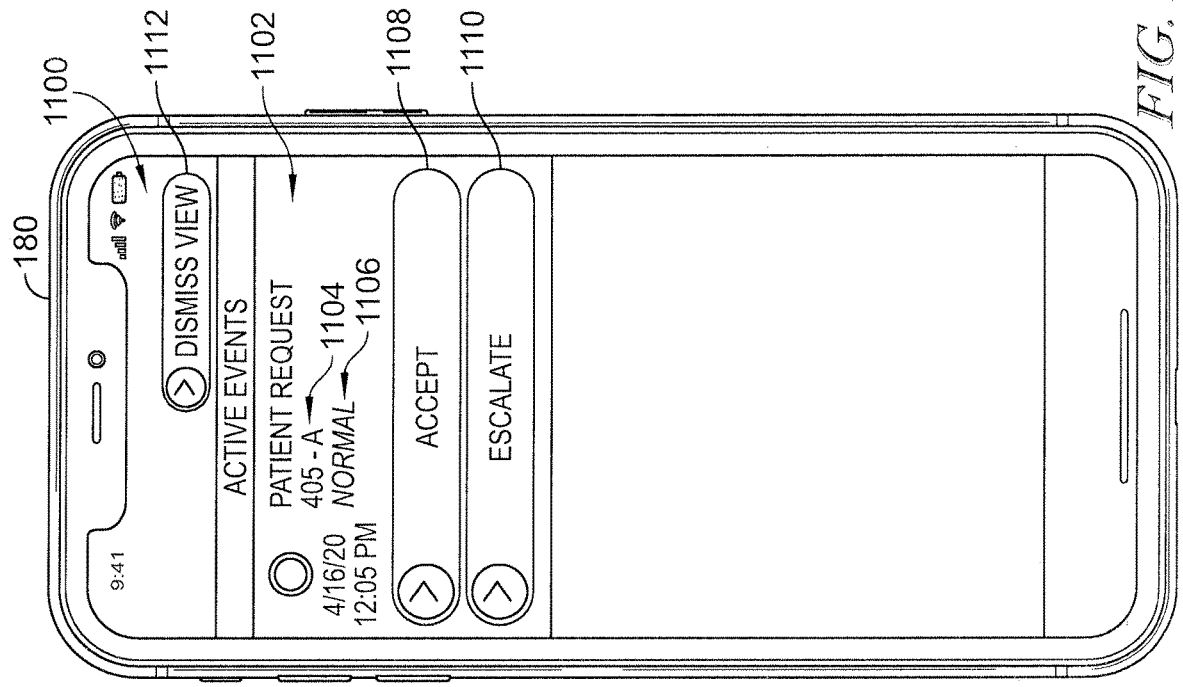
FIG. 11 is an embodiment of a graphical user interface that may be displayed by a caregiver communication device to enable a caregiver to respond to a received caregiver call request.

Turning to FIG. 11, the graphical user interface 1100 includes a patient request notification 1102, an identification 1104 of the location of the patient 150 (i.e., "405—A"), an identification 1106 of a priority assigned to the patient request, a selectable accept option 1108, a selectable escalate option 1110, and a selectable dismiss view option 1112. In the illustrative embodiments, any of the options 1108, 1110, 1112 may be selected by the caregiver 190 sliding their finger across the corresponding option 1108, 1110, 1112 (e.g., from left to right). In response to selection of the accept option 1108, the caregiver communication device 180 sends a notification to the system 100 (e.g., to the server compute devices 110, the EMR system 184, etc.) indicating that the caregiver 190 has accepted the request. Conversely, in response to the caregiver 190 selecting the escalate option 1110, the caregiver communication device 180 sends a notification to the system 100 (e.g., the server compute devices 110, the EMR system 184, etc.) indicating that the caregiver 190 has not accepted the request. In response, the system 100 notifies a backup caregiver (e.g., the caregiver 192) of the request by sending a corresponding message to the caregiver communication device 182 of the backup caregiver 192. In response to selection of the dismiss view option 1112, the caregiver communication device 180 displays a previously displayed graphical user interface (e.g., a graphical user interface that was displayed before the caregiver communication device 180 received the notification of the patient request).

Figure 12:
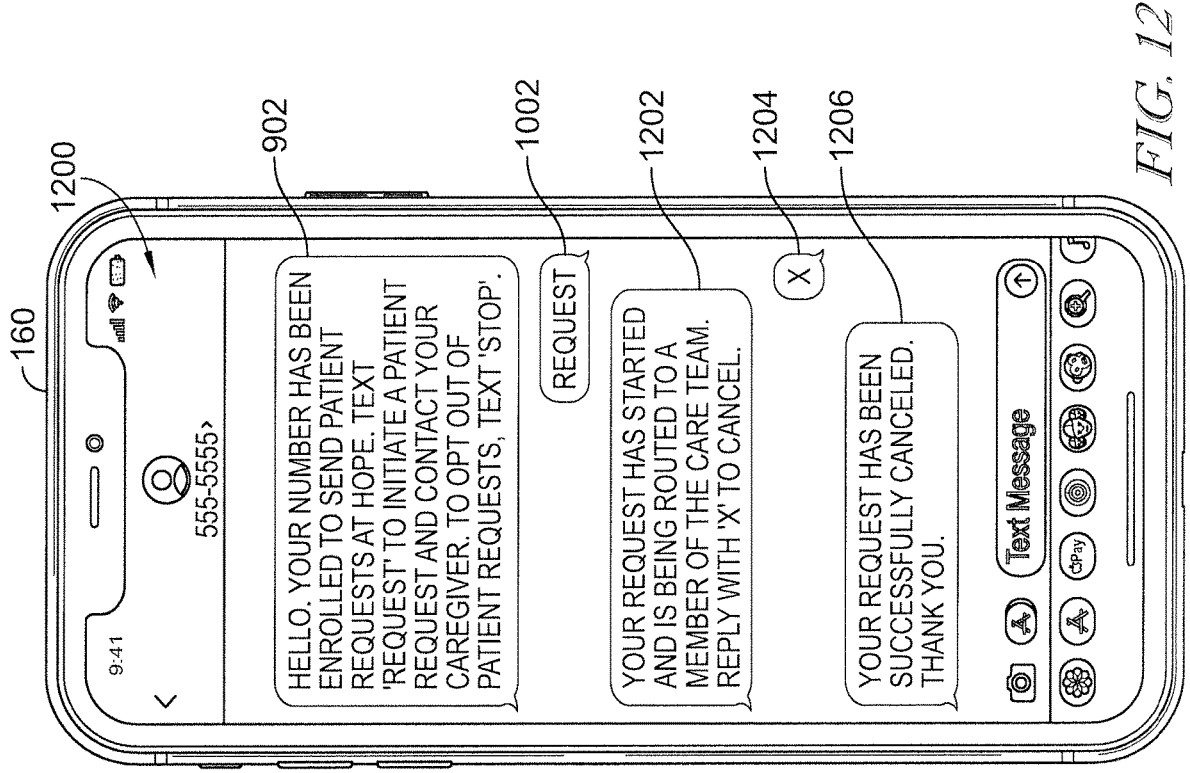
FIG. 12 is an embodiment of a graphical user interface that may be displayed by a patient mobile communication device to confirm processing of a request, to cancel the request, and to confirm cancellation of the request.

Referring now to FIG. 12, the mobile communication device 160 of the patient 150 displays a graphical user interface 1200, similar to the graphical user interfaces 900, 1000 subsequent to submission of the patient request. In the illustrative embodiment, the graphical user interface 1200 includes a representation 1202 of a message received from the system 100 (e.g., from the server compute device 110 operating in conjunction with the mobile services 170 and the EMR system 184) indicating that the request is being routed to a member of the patient care team. The representation 1202, in the illustrative embodiment, is displayed by the mobile communication device 160 of the patient 150 while the caregiver 190 views and responds to the graphical user interface 1100 displayed by the caregiver communication device 180. The graphical user interface 1200 additionally includes a representation 1204 indicating that the patient 150 subsequently submitted a text message containing the character "X" to cancel the patient request. Further, the user graphical user interface 1200 includes a representation 1206 of a confirmation message received from the system 100 confirming that the patient request has been cancelled.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected. There exist a plurality of advantages of the present disclosure arising from the various features of the apparatus, systems, and methods described herein. It will be noted that alternative embodiments of the apparatus, systems, and methods of the present disclosure may not include all of the features described, yet still benefit from at least some of the advantages of such features. Those of ordinary skill in the art may readily devise their own implementations of the apparatus, systems, and methods that incorporate one or more of the features of the present disclosure.

The invention claimed is:

1. A healthcare facility system comprising:
 a hospital having caregiver call hardware installed therein, the caregiver call hardware including a call request server configured to receive call requests placed by patients using call equipment in rooms of the hospital, the call equipment including patient beds having inputs that are usable to place call requests that are received by the call request server;
 a makeshift facility situated temporarily adjacent the hospital, the makeshift facility housing patients during periods of high patient population that exceeds a patient capacity of the hospital, the makeshift facility lacking caregiver call equipment and the makeshift facility including patient beds that are unable to send call requests to the call request server of the hospital;
 a plurality of caregiver communication devices, each caregiver communication device of the plurality of caregiver communication devices being assigned to a caregiver of the plurality of caregivers and being configured to receive call requests from patients of the hospital; and
 a mobile services server having circuitry configured to:
 store, based on commands from respective caregiver communication devices, patient mobile communication device information in response to the caregivers enrolling specific patient mobile communication devices for nurse call communications, the nurse call communications comprising short message service (SMS) messages sent from the patient mobile communication devices of patients in the makeshift facility;
 receive SMS messages sent from the patient mobile communication devices of patients in the makeshift facility;
 determine as a function of a mobile communication device identifier that includes a phone number of each of the patient mobile communication devices that sent each of the SMS messages, a respective caregiver to notify; and
 send, to one or more of the plurality of caregiver communication devices for display, the call requests placed by patients in the hospital using the call request equipment and the SMS messages sent by patients in the makeshift facility so that the call requests and SMS messages are displayed on the caregiver communication device of the respective caregiver.

2. The healthcare facility system of claim 1, wherein to determine, as a function of a mobile communication device identifier of the patient mobile communication device that sent each of the SMS messages, the caregiver to notify comprises to:
 determine a patient identifier that has been associated with the patient mobile communication device identifier; and
 determine the respective caregiver that has been associated with the patient identifier.

3. The healthcare facility system of claim 2, wherein the circuitry is further configured to determine the respective caregiver further as a function of one or more words in each of the received SMS messages.

4. The healthcare facility system of claim 3, wherein to determine the respective caregiver as a function of one or more words in each of the received SMS messages comprises to identify a predefined word in each of the received SMS messages that is associated with a corresponding caregiver.

5. The healthcare facility system of claim 3, wherein to determine the caregiver as a function of one or more words in each of the received SMS messages comprises to:
perform natural language processing on the one or more words to identify a type of requested assistance; and
identify a corresponding caregiver associated with the determined type of requested assistance.

6. The healthcare facility system of claim 1, wherein the circuitry is further configured to:
receive requests from each of the caregiver communication devices to enroll each patient authorized to request assistance via the SMS messages from the respective patient mobile communication device; and
enroll, in response to each of the requests, the respective patient.

7. The healthcare facility system of claim 6, wherein to receive the request to enroll a patient comprises to receive the request based on an SMS text message sent from the patient mobile communication device of the respective patient to be enrolled.

8. The healthcare facility system of claim 6, where to receive the request to enroll a patient comprises to receive the request based on an SMS text message sent from a mobile phone of a person other than the patient.

9. The healthcare facility system of claim 6, wherein to receive the request to enroll a patient comprises to receive a request to associate the phone number of the patient mobile communication device that sent the request with a patient identifier.

10. The healthcare facility system of claim 6, wherein to receive the request to enroll a patient comprises to receive a request that includes predefined text to associate an identifier of the patient mobile communication device with a patient identifier.

11. The healthcare facility system of claim 10, wherein to receive the request to enroll a patient comprises to receive a request in which the predefined text is one or more words that have been mapped to the patient identifier.

12. The healthcare facility system of claim 11, wherein to receive the request to enroll a patient comprises to receive a request in which the predefined text does not include the patient identifier.

13. The healthcare facility system of claim 6, wherein to enroll a patient comprises to associate a mobile communication device identifier with a patient identifier.

14. The healthcare facility system of claim 13, wherein to associate a mobile communication device identifier with a patient identifier comprises to associate, with the patient identifier, the phone number of the patient mobile communication device that sent the request to enroll the patient.

15. The healthcare facility system of claim 1, wherein the circuitry is further configured to confirm a caregiver call request contained withing each SMS message with the patient mobile communication device that sent the caregiver call request before sending, to the determined caregiver, a notification of the caregiver call request.

16. The healthcare facility system of claim 1, wherein the circuitry is further configured to send, to the patient mobile communication device that sent each SMS message, a confirmation that the respective caregiver has been notified.

17. The healthcare facility system of claim 1, wherein the circuitry is further configured to receive a caregiver call request based on a textual message sent with a messaging platform that is not SMS.

18. The healthcare facility system of claim 1, wherein the circuitry is further configured to:
receive a response from the caregiver; and
redirect, based on a determination that the response is indicative of a rejection, the request to a backup caregiver.

* * * * *